US012758680B2

(12) United States Patent
Ngai et al.

(10) Patent No.: US 12,758,680 B2
(45) Date of Patent: Oct. 13, 2026

(54) INJECTABLE MAGNESIUM OXYCHLORIDE CEMENT FOAM (MOCF)-DERIVED SCAFFOLD FOR TREATING OSTEOPOROTIC BONE DEFECTS

(71) Applicant: The Chinese University of Hong Kong, Shatin (CN)

(72) Inventors: To Ngai, Tai Wai (CN); Yuwei Zhu, Tai Po (CN); Ling Qin, Tai Po (CN); Jiankun Xu, Shatin (CN)

(73) Assignee: The Chinese University of Hong Kong, Shatin (CN)

( * ) Notice: Subject to any disclaimer, the term of this patent is extended or adjusted under 35 U.S.C. 154(b) by 469 days.

(21) Appl. No.: 18/371,369

(22) Filed: Sep. 21, 2023

(65) Prior Publication Data

US 2024/0108785 A1 Apr. 4, 2024

Related U.S. Application Data

(60) Provisional application No. 63/410,185, filed on Sep. 26, 2022.

(51) Int. Cl.

*A61L 27/04* (2006.01)
*A61L 27/12* (2006.01)
*A61L 27/22* (2006.01)

(52) U.S. Cl.

CPC ............. *A61L 27/047* (2013.01); *A61L 27/12* (2013.01); *A61L 27/222* (2013.01); *A61L 27/227* (2013.01); *A61L 2430/02* (2013.01)

(58) Field of Classification Search

CPC ...... A61L 27/047; A61L 27/12; A61L 27/222; A61L 27/227; A61L 2430/02; A61L 24/0036; A61L 24/02; A61L 27/56

See application file for complete search history.

(56) References Cited

U.S. PATENT DOCUMENTS 3,969,453 A * 7/1976 Thompson ................. C08J 9/40 106/676
4,055,519 A 10/1977 Thompson
(Continued)

FOREIGN PATENT DOCUMENTS

CN 104591679 A 5/2015
CN 111840652 A 10/2020
(Continued)

OTHER PUBLICATIONS

Zhu, et al. "Injectable magnesium oxychloride cement foam-derived scaffold for augmenting osteoporotic defect repair" Journal of Colloid and Interface Science, vol. 640, pp. 199-210 (Feb. 25, 2023).

(Continued)

*Primary Examiner* — Vi X Nguyen
(74) *Attorney, Agent, or Firm* — Kilpatrick Townsend & Stockton LLP

(57) ABSTRACT

Provided herein are magnesium oxychloride cement compositions having a micro-/macro-two-tier porous structure derived from a Pickering foam form of the compositions. The compositions include magnesium oxide, magnesium chloride, water, and one or more surface modifying agents that modify at least a portion of the magnesium oxide, thereby creating particulates sufficient for stabilizing the Pickering foam. Also provided are bone repair scaffolds, and methods for producing the provided compositions and scaffolds and using them to repair bone defects.

14 Claims, 7 Drawing Sheets

Specification includes a Sequence Listing.

(56) References Cited

U.S. PATENT DOCUMENTS

| | | | |
|---|---|---|---|
| 8,916,228 B2 | 12/2014 | Oh et al. | |
| 9,540,287 B2 | 1/2017 | Aldabaibeh et al. | |
| 2019/0134259 A1* | 5/2019 | Kronenthal | A61L 24/043 |

FOREIGN PATENT DOCUMENTS

| | | |
|---|---|---|
| CN | 111888521 A | 11/2020 |
| CN | 114601969 A | 6/2022 |
| WO | 2008/117043 A2 | 10/2008 |

OTHER PUBLICATIONS

International Search Report and Written Opinion for International Application No. PCT/CN2023/121109, mailed Dec. 12, 2023, 10 pages.

Guan, et al., "Effect of different-sizes of hydroxyapatite on the water resistance of magnesium oxychloride cement for bone repair," RSC Adv., vol. 9, pp. 38619-38628 (2019).

Tan, et al., "Synthesis and in vitro degradation of a novel magnesium oxychloride cement," J Biomed Mater Res A, vol. 103(1), pp. 194-202 (Jan. 2015).

Zhu, et al., "Poly (I-lactic acid) (PLLA) Coatings with Controllable Hierarchical Porous Structures on Magnesium Substrate: An Evaluation of Corrosion Behavior and Cytocompatibility," ACS Applied Bio Materials, vol. 2, pp. 3843-3853 (2019).

Zhu, et al.,"Poly (I-lactic acid) (PLLA)/MgSO4•7H2O Composite Coating on Magnesium Substrates for Corrosion Protection and Cytocompatibility Promotion," ACS Applied Bio Materials, vol. 3, pp. 1364-1373 (2020).

Tian, et al., "An innovative Mg/Ti Hybrid Fixation System Developed for Fracture Fixation and Healing Enhancement at Load-Bearing Skeletal Site," Biomaterials, vol. 180, pp. 173-183 (2018).

Sheng, et al., "Ultra-stable Aqueous Foams Induced by Interfacial Co-assembly of Highly Hydrophobic Particles and Hydrophilic Polymer," Journal of Colloid and Interface Science, vol. 579, pp. 628-636 (2020).

Zheng, et al., "Magnesium Facilitates The Healing of Atypical Femoral Fractures: A Single-cell Transcriptomic Study," Materials Today, vol. 52, pp. 43-62 (2022).

Walling, et al., "Magnesia-Based Cements: A Journey of 150 Years, and Cements for the Future?," Chem. Rev., vol. 116, 7, pp. 4170-4204 (2016).

* cited by examiner

INJECTABLE MAGNESIUM OXYCHLORIDE CEMENT FOAM (MOCF)-DERIVED SCAFFOLD FOR TREATING OSTEOPOROTIC BONE DEFECTS

CROSS-REFERENCE TO RELATED APPLICATIONS

The present application claims priority to U.S. Provisional Application No. 63/410,185 filed Sep. 26, 2022, the full disclosure of which is incorporated by reference in its entirety for all purposes.

REFERENCE TO A SEQUENCE LISTING

This application contains a Sequence Listing which has been submitted electronically in XML format and is hereby incorporated by reference in its entirety. Said XML copy, created on Aug. 20, 2026, is named 080015-1366156-035310US_ST26.xml, and is 11,315 bytes in size.

BACKGROUND

With the aging of the global population, osteoporosis is a highly prevalent health concern in today's society. In particular, frequent osteoporosis-related fractures, along with the delayed healing process for such fractures, cause major suffering for osteoporotic patients. Cement augmentation has been widely applied for treating osteoporotic bone defects. The current products for clinical therapies are mostly based on calcium phosphate (CaP) cements (CPCs), including hydroxyapatite and brushite. However, these materials can be only partially or minimally resorbed by the body due to a slow degradation rate for CPCs under physiological conditions. This slow degradation can induce poor integration with regenerated bone tissue and retard the formation of new bone. Worse still, inflammations may also occur as a result of long-lasting foreign implants.

Magnesium (Mg)-containing cements have been proposed as a promising alternative to the classic Ca-based cements. These Mg-based cements typically have a faster dissolution rate and better bonding ability to natural bone than seen with Ca-based cements. Even more encouragingly, Mg ions ($Mg^{2+}$) released from a degraded Mg-based cement can play a vital role in bone metabolism by activating bone-tissue-specific cell responses and regulating immunological reactions. Mg phosphate cements (MPCs) have been shown to stimulate specific cell and tissue responses and to actively drive the bone remodeling process. Nevertheless, exothermic reactions associated with the hardening process of MPC may induce necrosis of the surrounding tissues. Moreover, the release of ammonia or ammonium ions from an MPC, e.g., from struvite, into the physiological environment may cause biocompatibility issues.

Magnesium oxychloride cement (MOC, $xMg(OH)_2 \cdot yMgCl_2 \cdot zH_2O$), also known as Sorel cement, has received increasing attention as a bone grafting material. Although MOC has been diversely implemented in binder, flooring, and stucco as a construction material, it has been losing its popularity in such civil engineering applications due to poor water resistance and subsequent degradation. Surprisingly, these degradation tendencies offer reasons to expand applications of MOC in hard tissue engineering. Apart from osteoinductive $Mg^{2+}$ ions, which are eluted from a degrading MOC and can elicit osteogenesis and facilitate bony formation, chloride ions ($Cl^-$) eluted during MOC degradation also can play an essential role in bone homeostasis and commit to maintaining a dynamic balance in a physiological environment. In addition, MOC is characterized by a low-exothermic setting process, high early strength, and satisfactory plasticity, rendering it a suitable bone augmenting material.

While MOC has been intensively studied to develop fabrication strategies for improved water-resistance, mechanical strength, and crystal phase composition in producing ideal MOC-based construction materials, research on the use of MOC as an implantable scaffold to augment bone restoration are rare. Tan et al. conducted a preliminary study to assess the feasibility of MOC for orthopedic applications via co-culturing bone marrow stem cells (BMSCs) with MOC material (J. Biomed. Mater. Res. A 103, (2015): 194). Results demonstrated that MOC modified with orthophosphoric acid showed favorable physical properties, i.e., compressive strength and degradation kinetics, to be a bone grafting material, while supporting the attachment and growth of BMSCs. Later in 2019, Guan et al. investigated the influence of micro-sized and nano-sized hydroxyapatite (μ-HA and n-HA) particles on the water-resistance and biological performance of MOC in a preclinical rat shinbone defect model (RSC Adv. 9, (2019): 38619). They found that the addition of HA can effectively improve the water resistance of MOC, thus resulting in a reasonable resorption rate in vivo. Moreover, the MOC/n-HA combination posed a more positive osteogenic effect than an MOC/μ-HA combination. Notably, the MOC-based scaffolds presented in the reported work are all dense and non-porous, such that cell and tissue ingress into the scaffold may be hindered.

An ideal cement-derived implant is expected to present a hierarchical micro- and macro-porous structure for enabling cell and tissue attachment and ingress and sufficient nutrient transport. Though nano- and micro-porosity can be readily generated during cement formation, macro-porosity must be intentionally constructed. There are numerous available strategies to introduce macropores into a cement scaffold, including particulate leaching, three-dimensional (3D) printing, foaming, and emulsion-templating. Among these approaches, foaming offers the benefits of avoiding the use of large amount of porogen agents, and creating two-tier porosity desirable for cement implants. When applied in a cement scaffold, foaming techniques can also support good injectability and in-situ self-setting ability, enabling minimally invasive surgery.

To date, several foaming techniques have been successfully applied for hierarchical porous cement preparation, including gas foaming, syringe foaming, and surfactant foaming. However, these reported studies either involved multiple steps, or required the participation of elaborately selected biocompatible surface-active additives, thereby limiting clinical applications. Thus, more effective approaches are needed to introduce such hierarchical porosity into a cement-based scaffold without deteriorating the mechanical and biological performance. The present disclosure addresses these and other needs by providing materials and methods related to porous magnesium oxychloride cements having several beneficial advantages for use as bone repair scaffolds.

BRIEF SUMMARY

The present disclosure generally relates to a magnesium oxychloride cement (MOC) foam (MOCF)-derived three-dimensional (3D) porous scaffold produced by incorporating Pickering foaming techniques into a Mg oxide (MgO)-Mg chloride ($MgCl_2$)-water ($H_2O$) reaction system. The MOCF-derived scaffold provides several advantages particularly beneficial for the restoration of osteoporotic bone defects. In some embodiments, the provided materials and methods include light-burnt MgO microparticles modified with trace amount of propyl gallate. The modified microparticles serve as a particulate stabilizer to generate an ultra-stable foam, while a $MgCl_2$ aqueous solution serves as a continuous phase. The in-situ curing of the provided material can synchronously proceeded via reaction between MgO and the liquid phase, leading to the formation of a hierarchical porous MOCF scaffold in one step.

The resulting MOCF scaffold can display a desirable integration of micro- and macro-porosity, excellent handling performance, suitable degradation rate, and favorable mechanical performance. The provided MOCF scaffold can not only act as a structural support, but can also recruit mesenchymal stem cells (MSCs) and stimulate in-situ osteogenesis, owing to its cytotropic architecture of the MOCF-derived scaffold and the in-situ delivery of osteoinductive agents such as $Mg^{2+}$ ions. Substantial in vitro evidence has confirmed the superior bioactivity and osteoinductivity of the MOCF-derived scaffolds disclosed herein in comparison with commercially-available non-porous calcium deficient hydroxyapatite (CDHA) cement. These features render the disclosed materials and methods promising alternatives to CaP-based bone cement products for clinical applications, e.g., osteoporotic bone defect repair applications, with prominent curative efficacy.

In one aspect, the disclosure is to a composition that includes magnesium oxide, magnesium chloride, a surface modifying agent, and water. In some embodiments, the composition includes 15 wt % to 70 wt % of the magnesium oxide, 2 wt % to 10 wt % of the magnesium chloride, 0.2 wt % to 2 wt % of the surface modifying agent, and 20 wt % to 65 wt % of the water. The surface modifying agent present in the composition modifies at least a portion of the magnesium oxide, thereby creating particulates sufficient for stabilizing a Pickering foam form of the composition. In some embodiments, the composition has the form of a homogenous paste. In some embodiments, the composition has the form of a cement formed by curing the homogeneous paste such that the cement includes a plurality of micropores.

In another aspect, the disclosure is to a bone repair scaffold. The scaffold includes a cement as disclosed herein. In some embodiments, the scaffold further includes cells adhered to the cement.

In another aspect, the disclosure is to a method for producing a magnesium oxychloride cement. The method includes forming a mixture of magnesium oxide and a surface modifying agent dispersed in an aqueous magnesium chloride solution. The method further includes frothing the mixture under conditions sufficient to generate an aqueous foam. In some embodiments, the method further includes forming a homogeneous paste from the aqueous foam. In some embodiments, the method further includes curing the homogeneous paste to produce the magnesium oxychloride cement.

In another aspect, the disclosure is to a method of repairing a bone defect in a subject. The method includes implanting a bone repair scaffold as disclosed herein proximate to a bone defect in the subject.

DETAILED DESCRIPTION

I. General

Figure 1:
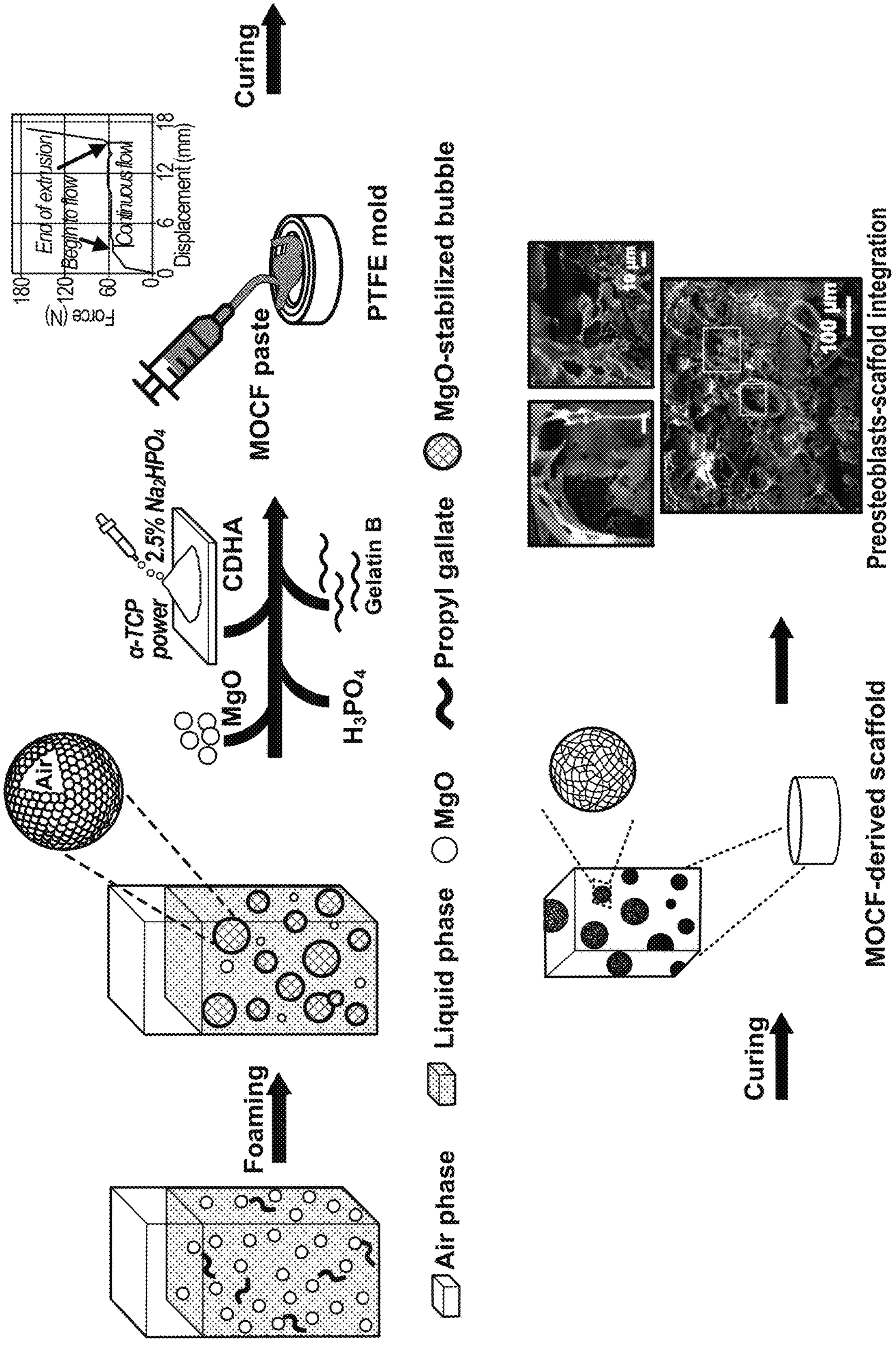
FIG. 1 is a schematic illustration of the fabrication of an injectable 3D porous magnesium oxychloride cement foam (MOCF)-derived scaffold in accordance with a provided embodiment, and demonstration of preosteoblasts-scaffold integration. An ultra-stable aqueous foam is fabricated first via high-speed frothing, where MgO microparticles adsorbed with trace amount of propyl gallate serve as a particulate stabilizer, and an $MgCl_2$ aqueous solution is the liquid phase. Residual additives are introduced to the ultra-stable foam to obtain an MOCF paste, which shows favorable injectability. After absolute curation in a mold, an MOCF scaffold with hierarchical porosity is obtained, where clear cellular infiltration of the scaffold, and excellent cell-scaffold integration, can be readily achieved.

The present disclosure provides an effectual and facile strategy to fabricate an injectable three-dimensional (3D) porous magnesium oxychloride cement (MOC) foam (MOCF)-derived scaffold by incorporating a Pickering foaming technique into the MOC formation process (FIG. 1). The provided MOCF-derived scaffolds are particularly advantageous for treating osteoporotic bone defect. Through one-step Pickering foaming, both macro- and micro-porosity structures are created within the scaffold to meet essential requirements allowing the scaffolds to function as bone substitutes for bone defect repair. The as-fabricated MOCF scaffold displays excellent handling performance in the paste state, while also exhibiting sufficient load-bearing capacity after solidification. In comparison with the traditional bone cement, calcium deficient hydroxyapatite (CDHA), the provided porous MOCF scaffold demonstrates a much higher biodegradation tendency and better cell recruitment ability. Additionally, bioactive ions eluted by MOCF create and sustain a biologically inductive microenvironment, in which in vitro osteogenesis is significantly enhanced. Together, these characteristics give the materials and methods disclosed herein great potential as improved alternatives to those instead using existing calcium-based products for augmenting osteoporotic bone regeneration. Moreover, this disclosure also provides a straightforward and efficient manufacturing strategy to construct bio-scaffolds with tailorable 3D porosity to meet clinical requirements for bone regeneration or other diverse applications.

II. Compositions

In one aspect, the present disclosure provides various magnesium oxychloride cement compositions that generally include magnesium oxide, magnesium chloride, one or more surface modifying agents, and water. In some embodiments, the composition comprises magnesium oxide, magnesium chloride, one or more surface modifying agents, and water. In some embodiments, the composition consists of magnesium oxide, magnesium chloride, one or more surface modifying agents, and water. In some embodiments, the composition consists essentially of magnesium oxide, magnesium chloride, one or more surface modifying agents, and water. The particular combination and relative amounts of these components allow the compositions to provide several surprising improvements in various important structural, mechanical, and biological characteristics. These improved characteristics are particularly advantageous when the provided compositions are used in the fabrication of certain medical implants, most notably scaffolds useful for treating osteoporotic bone defects.

The presence of the surface modifying agent in the provided compositions allows the compositions to form Pickering foams under the conditions disclosed herein. A Pickering foam is a foam that is stabilized by solid particles that adsorb onto the interface between the liquid and gas phases of the foam. In the provided compositions, the surface modifying agent acts on at least a portion of the magnesium oxide in the composition, creating particulates of magnesium oxide capable of stabilizing the foam. Upon curing of the stabilized foam or a homogeneous paste form thereof into a cement, the air bubbles of the foam create voids in the resulting cement, generating the desired cement porosity characteristics beneficial for implant scaffold applications. Accordingly, the identity and the amount of the surface modifying agent in the compositions are generally selected such that the surface modifying agent is effective in modifying the magnesium oxide to create the particulates sufficient for stabilizing the Pickering foam.

The compositions disclosed herein can each include only one type of surface modifying agent, or can include two or more different surface modifying agents. In some embodiments, at least one surface modifying agent of the composition is a short-chain amphiphilic compound. In some embodiments, each surface modifying agent of the composition is a short-chain amphiphilic compound. In some embodiments, the surface modifying agents include or consist of one or more gallate compounds. In some embodiments, the surface modifying agents include or consist of one or more alkyl gallates.

In some embodiments, the surface modifying agents include or consist of propyl gallate. In some embodiments, the surface modifying agents include or consist of gallic acid. In some embodiments, the surface modifying agents include or consist of one or more straight chain saturated fatty acids. In some embodiments, the surface modifying agents include or consist of hexanoic acid. In some embodiments, the surface modifying agents include or consist of propyl gallate and hexanoic acid. In some embodiments, the surface modifying agents include or consist of propyl gallate and gallic acid. In some embodiments, the surface modifying agents include or consist of hexanoic acid and gallic acid. In some embodiments, the surface modifying agents include or consist of propyl gallate, hexanoic acid, and gallic acid.

The combined amount of the one or more surface modifying agents in the composition can be selected such that the amount is effective in modifying a sufficient portion of the magnesium oxide of the composition to create enough particulates to stabilize a Pickering foam form of the composition. The concentration of surface modifying agents in the composition can be, for example, between about 0.2 wt % and about 2 wt %, e.g., between 15 about 0.2 wt % and about 1.2 wt %, between about 0.4 wt % and about 1.4 wt %, between about 0.6 wt % and about 1.6 wt %, between about 0.8 wt % and about 1.8 wt %, or between about 1 wt % and about 2 wt %. In some embodiments, the surface modifying agent concentration in the composition is between about 0.4 wt % and about 1.3 wt %, e.g., between about 0.4 wt % and about 0.9 wt %, between about 0.5 wt % and about 1 wt %, between about 0.6 wt % and about 1.1 wt %, between about 0.7 wt % and about 1.2 wt %, or between about 0.8 wt % and about 1.3 wt %. In terms of lower limits, the surface modifying agent concentration in the composition can be, for example at least about 0.2 wt %, e.g., at least about 0.4 wt %, at least about 0.5 wt %, at least about 0.6 wt %, at least about 0.7 wt %, at least about 0.8 wt %, at least about 0.9 wt %, at least about 1 wt %, at least about 1.1 wt %, at least about 1.2 wt %, at least about 1.3 wt %, at least about 1.4 wt %, at least about 1.6 wt %, or at least about 1.8 wt %. In terms of upper limits, the surface modifying agent concentration in the composition can be, for example, at most about 2 wt %, e.g., at most about 1.8 wt %, at most about 1.6 wt %, at most about 1.4 wt %, at most about 1.3 wt %, at most about 1.2 wt %, at most about 1.1 wt %, at most about 1 wt %, at most about 0.9 wt %, at most about 0.8 wt %, at most about 0.7 wt %, at most about 0.6 wt %, at most about 0.5 wt %, or at most about 0.4 wt %. Higher surface modifying agent concentrations, e.g., greater than about 2 wt %, and lower surface modifying agent concentrations, e.g., less than about 0.2 wt %, are also contemplated.

The magnesium oxide content of the composition can be selected to provide enough magnesium oxide to be modified and form sufficient particulates to stabilize a Pickering foam form of the composition. Because the crystal phase of a magnesium oxychloride cement depends at least in part on the amount of magnesium oxide relative to the amounts of magnesium chloride and water in the cement, and because the cement crystal phase can influence important characteristics of the cement, the magnesium oxide content of the composition can also be selected to provide a cement formed from the composition with a desired crystal phase content. Accordingly, the inventors have demonstrated for this and other reasons that certain magnesium oxide concentrations provide the composition with advantageous physical, mechanical, and processing properties.

The concentration of the magnesium oxide in the composition can be, for example, between about 15 wt % and about 70 wt %, e.g., between about 15 wt % and about 48 wt %, between about 20.5 wt % and about 53.5 wt %, between about 26 wt % and about 59 wt %, between about 31.5 wt % and about 64.5 wt %, or between about 37 wt % and about 70 wt %. In some embodiments, the magnesium oxide concentration in the composition is between about 30 wt % and about 60 wt %, e.g., between about 30 wt % and about 48 wt %, between about 33 wt % and about 51 wt %, between about 36 wt % and about 54 wt %, between about 39 wt % and about 57 wt %, or between about 42 wt % and about 60 wt %. In terms of lower limits, the magnesium oxide concentration in the composition can be, for example, at least about 15 wt %, e.g., at least about 20.5 wt %, at least about 26 wt %, at least about 30 wt %, at least about 33 wt %, at least about 36 wt %, at least about 39 wt %, at least about 42 wt %, at least about 45 wt %, at least about 48 wt %, at least about 51 wt %, at least about 54 wt %, at least about 57 wt %, at least about 60 wt %, or at least about 64.5 wt %. In terms of upper limits, the magnesium oxide concentration in the composition can be, for example, at most about 70 wt %, e.g., at most about 64.5 wt %, at most about 60 wt %, at most about 57 wt %, at most about 54 wt %, at most about 51 wt %, at most about 48 wt %, at most about 45 wt %, at most about 42 wt %, at most about 39 wt %, at most about 36 wt %, at most about 33 wt %, at most about 30 wt %, at most about 26 wt %, or at most about 20.5 wt %. Higher magnesium oxide concentrations, e.g., greater than about 70 wt %, and lower magnesium oxide concentrations, e.g., less than about 15 wt %, are also contemplated.

As with the magnesium oxide, the inventors have also shown that the magnesium chloride content of the composition can be selected to provide a cement formed from the composition with a desired crystal phase content and other advantageous physical, mechanical, and processing properties. The concentration of the magnesium chloride in the composition can be, for example, between about 2 wt % and about 10 wt %, e.g., between about 2 wt % and about 6.8 wt %, e.g., between about 2.8 wt % and about 7.6 wt %, between about 3.6 wt % and about 8.4 wt %, between about 4.4 wt % and about 9.2 wt %, or between about 5.2 wt % and about 10 wt %. In some embodiments, the magnesium chloride concentration in the composition is between about 4 wt % and about 8 wt %, e.g., between about 4 wt % and about 6.4 wt %, between about 4.4 wt % and about 6.8 wt %, between about 4.8 wt % and about 7.2 wt %, between about 5.2 wt % and about 7.6 wt %, or between about 5.6 wt % and about 8 wt %. In terms of lower limits, the magnesium chloride concentration in the composition can be, for example, at least about 2 wt %, e.g., at least about 2.8 wt %, at least about 3.6 wt %, at least about 4 wt %, at least about 4.4 wt %, at least about 4.8 wt %, at least about 5.2 wt %, at least about 5.6 wt %, at least about 6 wt %, at least about 6.4 wt %, at least about 6.8 wt %, at least about 7.2 wt %, at least about 7.6 wt %, at least about 8 wt %, at least about 8.4 wt %, or at least about 9.2 wt %. In terms of upper limits, the magnesium chloride concentration in the composition can be, for example, at most about 10 wt %, e.g., at most about 9.2 wt %, at most about 8.4 wt %, at most about 8 wt %, at most about 7.6 wt %, at most about 7.2 wt %, at most about 6.8 wt %, at most about 6.4 wt %, at most about 6 wt %, at most about 5.6 wt %, at most about 5.2 wt %, at most about 4.8 wt %, at most about 4.4 wt %, at most about 4 wt %, at most about 3.6 wt %, or at most about 2.8 wt %. Higher magnesium chloride concentrations, e.g., greater than about 10 wt %, and lower magnesium chloride concentrations, e.g., less than about 2 wt %, are also contemplated.

The water content of the composition can also be selected to provide a cement formed from the composition with a desired crystal phase content and other advantageous physical, mechanical, and processing properties. The concentration of the water in the composition can be, for example, between about 20 wt % and about 65 wt %, e.g., between about 20 wt % and about 47 wt %, between about 24.5 wt % and about 51.5 wt %, between about 29 wt % and about 56 wt %, between about 33.5 wt % and about 60.5 wt %, or between about 38 wt % and about 65 wt %. In some embodiments, the water concentration in the composition is between about 30 wt % and about 55 wt %, e.g., between about 30 wt % and about 45 wt %, between about 32.5 wt % and about 47.5 wt %, between about 35 wt % and about 50 wt %, between about 37.5 wt % and about 52.5 wt %, or between about 40 wt % and about 55 wt %. In terms of lower limits, the water concentration in the composition can be, for example at least about 20 wt %, e.g., at least about 24.5 wt %, at least about 29 wt %, at least about 32.5 wt %, at least about 35 wt %, at least about 37.5 wt %, at least about 40 wt %, at least about 42.5 wt %, at least about 45 wt %, at least about 47.5 wt %, at least about 50 wt %, at least about 52.5 wt %, at least about 56 wt %, or at least about 60.5 wt %. In terms of upper limits, the water concentration in the composition can be, for example, at most about 65 wt %, e.g., at most about 60.5 wt %, at most about 56 wt %, at most about 52.5 wt %, at most about 50 wt %, at most about 47.5 wt %, at most about 45 wt %, at most about 42.5 wt %, at most about 40 wt %, at most about 37.5 wt %, at most about 35 wt %, at most about 32.5 wt %, at most about 29 wt %, or at most about 24.5 wt %. Higher water concentrations, e.g., greater than about 65 wt %, and lower water concentrations, e.g., less than about 20 wt %, are also contemplated.

The particularly useful properties of the provided composition have been demonstrated to be the result not only of the separate concentrations of individual components of the composition, but also of the amounts of the components in relation to one another. For example, certain relative amounts of the magnesium oxide with respect to the magnesium chloride provide the composition with its advantageous features. The molar ratio of the magnesium oxide in the composition to the magnesium chloride in the composition can be, for example, between about 2.5:1 and about 15:1, e.g., between about 2.5:1 and about 10:1, between about 3.75:1 and about 11.25:1, between about 5:1 and about 12.5:1, between about 6.25:1 and about 13.75:1, or between about 7.5:1 and about 15:1. In terms of lower limits, the molar ratio of the magnesium oxide to the magnesium chloride can be, for example, at least about 2.5:1, e.g., at least about 3.75:1, at least about 5:1, at least about 6.25:1, at least about 7.5:1, at least about 8.75:1, at least about 10:1, at least about 11.25:1, at least about 12.5:1, or at least about 13.75:1. In terms of upper limits, the molar ratio of the magnesium oxide to the magnesium chloride can be, for example, at most about 15:1, e.g., at most about 13.75:1, at most about 12.5:1, at most about 11.25:1, at most about 10:1, at most about 8.75:1, at most about 7.5:1, at most about 6.25:1, at most about 5:1, or at most about 3.75:1. Higher ratios of magnesium oxide to magnesium chloride, e.g., greater than about 15:1, and lower ratios, e.g., less than about 2.5:1, are also contemplated.

Certain relative amounts of the water in the composition to the magnesium chloride have also been demonstrated as providing the compositions disclosed herein with their surprisingly useful properties. The molar ratio of the water in the composition to the magnesium chloride in the composition can be, for example, between about 5:1 and about 25:1, e.g., between about 5:1 and about 17:1, between about 7:1 and about 19:1, between about 9:1 and about 21:1, between about 11:1 and about 23:1, or between about 13 and about 25:1. In terms of lower limits, the molar ratio of the water to the magnesium chloride can be, for example, at least about 5:1, e.g., at least about 7:1, at least about 9:1, at least about 11:1, at least about 13:1, at least about 15:1, at least about 17:1, at least about 19:1, at least about 21:1, or at least about 23:1. In terms of upper limits, the molar ratio of the water to the magnesium chloride can be, for example, at most about 25:1, e.g., at most about 23:1, at most about 21:1, at most about 19:1, at most about 17:1, at most about 15:1, at most about 13:1, at most about 11:1, at most about 9:1, or at most about 7:1. Higher ratios of water to magnesium chloride, e.g., greater than about 25:1, and lower ratios, e.g., less than about 5:1, are also contemplated.

The compositions disclosed herein can also include one or more additional compounds shown to provide the compositions with beneficial properties such as increased mechanical strength and/or improved handling performance during processing or application. In some embodiments, such additives are introduced to the composition after a Pickering foam form of the composition has been formed. In some embodiments, the one or more additives are introduced to the composition before or as the composition is mixed to generate a homogeneous paste form of the composition.

In some embodiments, the composition further includes as additives one or more soluble phosphate compounds. In some embodiments, the composition includes phosphoric acid. In some embodiments, the composition includes sodium dihydrogen phosphate. In some embodiments, the composition includes disodium hydrogen phosphate. In some embodiments, the composition includes phosphoric acid and sodium dihydrogen phosphate. In some embodiments, the composition includes phosphoric acid and disodium hydrogen phosphate. In some embodiments, the composition includes phosphoric acid, sodium dihydrogen phosphate, and disodium hydrogen phosphate.

The total concentration of the one or more soluble phosphate compounds in the provided composition, when present in the composition, can be, for example, between about 0.1 wt % and about 2 wt %, e.g., between about 0.1 wt % and about 0.6 wt %, between about 0.15 wt % and about 0.8 wt %, between about 0.2 wt % and about 1.1 wt %, between about 0.25 wt % and about 1.5 wt %, or between about 0.35 wt % and about 2 wt %. In terms of lower limits, the soluble phosphate compound concentration in the composition can be, for example, at least about 0.1 wt %, e.g., at least about 0.15 wt %, at least about 0.2 wt %, at least about 0.25 wt %, at least about 0.35 wt %, at least about 0.45 wt %, at least about 0.6 wt %, at least about 0.8 wt %, at least about 1.1 wt %, or at least about 1.5 wt %. In terms of upper limits, the soluble phosphate compound concentration in the composition can be, for example, at most about 2 wt %, e.g., at most about 1.5 wt %, at most about 1.1 wt %, at most about 0.8 wt %, at most about 0.6 wt %, at most about 0.45 wt %, at most about 0.35 wt %, at most about 0.25 wt %, at most about 0.2 wt %, or at most about 0.15 wt %. Higher soluble phosphate compound concentrations, e.g., greater than about 2 wt %, and lower soluble phosphate compound concentrations, e.g., less than about 0.1 wt %, are also contemplated.

In some embodiments, the composition further includes as additives one or more polymers. Without being bound by a particular theory, the inventors believe that polymers within the provided composition can act to crosslink the inorganic species of the composition. Such crosslinking can enhance the cohesive performance of the composition, allowing the composition to maintain a desired predetermined shape in an aqueous environment while the composition is in a paste form and while undergoing curing to form a cement. In some embodiments, the composition includes one or more natural polymers. In some embodiments, the composition includes gelatin. In some embodiments, the composition includes chitosan. In some embodiments, the composition includes gelatin and chitosan.

The total concentration of the one or more polymers such as gelatin and/or chitosan in the provided composition, when present in the composition, can be, for example, between about 1 wt % and about 10 wt %, e.g., between about 1 wt % and about 6.4 wt %, between about 1.9 wt % and about 7.3 wt %, between about 2.8 wt % and about 8.2 wt %, between about 3.7 wt % and about 9.1 wt %, or between about 4.6 wt % and about 10 wt %. In terms of lower limits, the polymer concentration in the composition can be, for example, at least about 1 wt %, e.g., at least about 1.9 wt %, at least about 2.8 wt %, at least about 3.7 wt %, at least about 4.6 wt %, at least about 5.5 wt %, at least about 6.4 wt %, at least about 7.3 wt %, at least about 8.2 wt %, or at least about 9.1 wt %. In terms of upper limits, the polymer concentration in the composition can be, for example, at most about 10 wt %, e.g., at most about 9.1 wt %, at most about 8.2 wt %, at most about 7.3 wt %, at most about 6.4 wt %, at most about 5.5 wt %, at most about 4.6 wt %, at most about 3.7 wt %, at most about 2.8 wt %, or at most about 1.9 wt %. Higher polymer concentrations, e.g., greater than about 10 wt %, and lower polymer concentrations, e.g., less than about 1 wt %, are also contemplated.

In some embodiments, the provided composition further includes as additives one or more calcium phosphate cements. In addition to increasing the mechanical strength of the composition, the calcium phosphate cements can allow the composition to beneficially elute calcium ions during in vivo degradation, further creating a biologically inductive microenvironment for supporting cell growth. In some embodiments, the composition includes calcium-deficient hydroxyapatite. In some embodiments, the composition includes hydroxyapatite. In some embodiments, the composition includes brushite. In some embodiments, the composition includes calcium-deficient hydroxyapatite and hydroxyapatite. In some embodiments, the composition includes calcium-deficient hydroxyapatite and brushite. In some embodiments, the composition includes hydroxyapatite and brushite. In some embodiments, the composition includes calcium-deficient hydroxyapatite, hydroxyapatite, and brushite.

The total concentration of the one or more calcium phosphate cements in the provided composition, when present in the composition, can be, for example, between about 10 wt % and about 35 wt %, e.g., between about 10 wt % and about 25 wt %, between about 12.5 wt % and about 27.5 wt %, between about 15 wt % and about 30 wt %, between about 17.5 wt % and about 32.5 wt %, or between about 20 wt % and about 35 wt %. In terms of lower limits, the calcium phosphate cement concentration in the composition can be, for example, at least about 10 wt %, e.g., at least about 12.5 wt %, at least about 15 wt %, at least about 17.5 wt %, at least about 20 wt %, at least about 22.5 wt %, at least about 25 wt %, at least about 27.5 wt %, at least about 30 wt %, or at least about 32.5 wt %. In terms of upper limits, the calcium phosphate cement concentration in the composition can be, for example, at most about 35 wt %, e.g., at most about 32.5 wt %, at most about 30 wt %, at most about 27.5 wt %, at most about 25 wt %, at most about 22.5 wt %, at most about 20 wt %, at most about 17.5 wt %, at most about 15 wt %, or at most about 12.5 wt %. Higher calcium phosphate cement concentrations, e.g., greater than about 35 wt %, and lower calcium phosphate cement concentrations, e.g., less than about 10 wt %, are also contemplated.

One of the advantages of the provided composition is that, because the composition can form a Pickering foam including a plurality of stable air bubbles, a cured cement form of the foam includes a plurality and variety of pores at the prior locations of those air bubbles. The number and morphology of the pores has been shown to be highly beneficial for applications such as bone defect repair, where the pores support the attachment and ingress of cells, and the transport of nutrients to the defect site. Unlike other, denser, cements such as calcium phosphate cements, the cement forms of the provided composition include not only nanopores, but also micropores and macropores, i.e., pores having a diameter greater than 10 μm. The percentage of the plurality of pores in a cement form of the provided composition having a diameter greater than 10 μm can be, for example, at least about 90%, e.g., at least about 91%, at least about 92%, at least about 93%, at least about 94%, at least about 95%, at least about 96%, at least about 97%, at least about 98%, or at least about 99%. The percentage of the plurality of pores in a cement form of the provided composition having a diameter greater than 50 μm can be, for example, at least about 10%, e.g., at least about 15%, at least about 20%, at least about 25%, at least about 30%, at least about 35%, at least about 40%, at least about 45%, at least about 50%, or at least about 55%.

Another advantage of the provided composition is that, because of the particular amounts of the magnesium oxide, magnesium chloride, and water in the composition, a desirable predetermined relative portion of phase 5 crystals in the composition can be attained. Magnesium oxychloride cements are based on chemical reactions between their magnesium oxide, magnesium chloride, and water components, producing different crystal phases having the general formula $xMg(OH)_2 \cdot yMgCl_2 \cdot zH_2O$. The particular values of x, y, and z in this formula depend at least in part on the initial molar ratios of the three precursor components. The phase 5 crystal phase of magnesium oxychloride cement has the formula $5Mg(OH)_2 \cdot MgCl_2 \cdot 8H_2O$ and contributes more than any other crystal phase to improved mechanical strength of the cement. The provided compositions advantageously result in magnesium oxychloride cements for which the phase 5 crystal phase predominates. The percentage of the magnesium oxychloride cement crystals in the provided composition that are phase 5 magnesium oxychloride cement crystals can be, for example, between about 70% and about 100%, e.g., between about 70% and about 88%, between about 73% and about 91%, between about 76% and about 94%, between about 79% and about 97%, or between about 82% and about 100%. In terms of lower limits, the percentage of the MOC crystals that are phase 5 crystals can be at least about 70%, e.g., at least about 73%, at least about 76%, at least about 79%, at least about 82%, at least about 85%, at least about 88%, at least about 91%, at least about 94%, or at least about 97%.

III. Bone Repair Scaffolds

Another aspect of the present disclosure relates to a scaffold useful for bone repair. The bone repair scaffold includes a magnesium oxide cement having any of the compositions disclosed herein. Because the scaffold includes a cement having a provided composition, the scaffold has the desirable characteristics of good biocompatibility, easy molding, good degradation, beneficial osteoconductivity, large pore size and high porosity, and excellent mechanical strength. Additionally, the particular makeup of the provided composition allows the composition to be easily processed into a variety of sizes and shapes, e.g., structures useful for bone repair applications. Further, the degradation products of the scaffold promote cell adherence, growth, and differentiation, yet pose little negative side effects for an implantation subject. The advantageous scaffold pore size and porosity resulting from the ability of the composition to form a Pickering foam allows for good mass transport of nutrients and other factors required by new bone formation. Moreover, the excellent mechanical strength of the scaffold can allow it to hold the structure of a tissue layer during vascularization and bony regeneration.

In some embodiments, cells are adhered to an exterior or interior surface of the cement of the provided scaffold. In some embodiments, cells are within pores of the provided scaffold. The cells can migrate to the scaffold from within the body of the subject, or can be seeded onto or within the scaffold prior to or subsequent to implantation in a subject. In some embodiments, one or more cell types promoting bone repair are adhered to or are within the scaffold. In some embodiments, mesenchymal stem cells are adhered to or are within the scaffold. In some embodiments, osteoblasts are adhered to or are within the scaffold. In some embodiments, fibroblasts are adhered to or are within the scaffold. In some embodiments, endothelial cells are adhered to or are within the scaffold. In some embodiments, mesenchymal stem cells and osteoblasts are adhered to or are within the scaffold. In some embodiments, mesenchymal stem cells and fibroblasts are adhered to or are within the scaffold. In some embodiments, mesenchymal stem cells and endothelial cells are adhered to or are within the scaffold. In some embodiments, osteoblasts and fibroblasts are adhered to or are within the scaffold. In some embodiments, osteoblasts and endothelial cells are adhered to or are within the scaffold. In some embodiments, fibroblasts and endothelial cells are adhered to or are within the scaffold. In some embodiments, mesenchymal stem cells, osteoblasts, and fibroblast are adhered to or are within the scaffold. In some embodiments, mesenchymal stem cells, osteoblasts, and endothelial cells are adhered to or are within the scaffold. In some embodiments, mesenchymal stem cells, fibroblasts, and endothelial cells are adhered to or are within the scaffold. In some embodiments, osteoblasts, fibroblasts, and endothelial cells are adhered to or are within the scaffold. In some embodiments, mesenchymal stem cells, osteoblasts, fibroblasts, and endothelial cells are adhered to or are within the scaffold.

IV. Methods for Producing Compositions and Scaffolds

Another aspect of the present disclosure relates to methods for producing the provided compositions and scaffolds. The particular combinations of steps of the methods have been shown to impart the compositions and scaffolds with the advantageous features discussed above. The methods generally include forming a mixture of magnesium oxide and one or more surface modifying agents dispersed in an aqueous magnesium chloride solution. In some embodiments, the methods further include selecting the identity of the one or more surface modifying agents, and the amounts of one or more of the magnesium oxide, the surface modifying agents, and the magnesium chloride and water in the aqueous magnesium chloride solution.

The identity and amount of the one or more surface modifying agents in the formed mixture can be as discussed above regarding the provided compositions. For example, the formed mixture can include between 0.2 wt % and 2 wt % of the surface modifying agents, and the surface modifying agents can include one or more short-chain amphiphilic compounds, e.g., propyl gallate, hexanoic acid, gallic acid, or any combination thereof. The amount of the magnesium oxide in the formed mixture can be as discussed above regarding the provided compositions. For example, the formed mixture can include between 15 wt % and 70 wt % of the magnesium oxide. The amount of the magnesium chloride in the formed mixture can be as discussed above regarding the provided compositions. For example, the formed mixture can include between 2 wt % and 10 wt % of the magnesium chloride.

The methods further include frothing the mixture under conditions sufficient to generate an aqueous foam. Preferably, the aqueous foam is a Pickering foam stabilized by particulates of the magnesium oxide modified by the surface modifying agents. The frothing of the mixture to create the foam generates stable air bubbles that define the pores of a cement formed by curing a paste form of the foam. In some embodiments, the method includes a step of selecting one or more conditions of the frothing, such that the selections are sufficient for formation of the aqueous foam.

The conditions of the frothing can include an agitation rate that is, for example, between about 6000 rpm and about 20,000 rpm, e.g., between about 6000 rpm and about 12,000 rpm, between about 6800 rpm and about 14,000 rpm, between about 7600 rpm and about 16,000 rpm, between about 8600 rpm and about 18,000 rpm, or between about 9700 rpm and about 20,000 rpm. In terms of lower limits, the agitation rate of the frothing can be at least about 6000 rpm, e.g., at least about 6800 rpm, at least about 7600 rpm, at least about 8600 rpm, at least about 9700 rpm, at least about 11,000 rpm, at least about 12,000 rpm, at least about 14,000 rpm, at least about 16,000 rpm, or at least about 18,000 rpm. In terms of upper limits, the agitation rate of the frothing can be, for example, at most about 20,000 rpm, e.g., at most about 18,000 rpm, at most about 16,000 rpm, at most about 14,000 rpm, at most about 12,000 rpm, at most about 11,000 rpm, at most about 9700 rpm, at most about 8600 rpm, at most about 7600 rpm, or at most about 6800 rpm. Higher agitation rates, e.g., greater than about 20,000 rpm, and lower agitation rates, e.g., less than about 6000 rpm, are also contemplated.

The conditions of the frothing can include a duration that is, for example, between about 10 seconds and about 60 seconds, e.g., between about 10 seconds and about 40 seconds, between about 15 seconds and about 45 seconds, between about 20 seconds and about 50 seconds, between about 25 seconds and about 55 seconds, or between about 30 seconds and about 60 seconds. In terms of lower limits, the duration of the frothing can be, for example, at least about 10 seconds, e.g., at least about 15 seconds, at least about 20 seconds, at least about 25 seconds, at least about 30 seconds, at least about 35 seconds, at least about 40 seconds, at least about 45 seconds, at least about 50 seconds, or at least about 55 seconds. In terms of upper limits, the duration of the frothing can be, for example, at most about 60 seconds, e.g., at most about 55 seconds, at most about 50 seconds, at most about 45 seconds, at most about 40 seconds, at most about 35 seconds, at most about 30 seconds, at most about 25 seconds, at most about 20 seconds, or at most about 15 seconds. Longer durations, e.g., more than about 60 seconds, and shorter durations, e.g., less than about 10 seconds, are also contemplated.

In some embodiments, the method further includes a step of mixing one or more additives into the aqueous foam. The identity and amounts of the additives, and the conditions of the mixing are generally sufficient to transform the aqueous foam to a homogenous paste. In some embodiments, the method further includes a step of selecting the identity of the one or more additives, the independent amounts of one or more of the additives, and/or one or more conditions of the mixing, such that the selections are sufficient to produce the homogeneous paste form of the composition.

The additives can be any of those disclosed herein. In some embodiments, the one or more additives include one or more soluble phosphate compounds, one or more polymers, one or more calcium phosphate cements, additional magnesium oxide, or any combination thereof. The identity and amount of the one or more soluble phosphate compounds mixed into the aqueous foam as additives can be as discussed above regarding the provided compositions. For example, the additives can include between about 0.2 wt % and about 2 wt % of the soluble phosphate compounds, and the soluble phosphate compounds can include phosphoric acid, sodium dihydrogen phosphate, disodium hydrogen phosphate, or any combination thereof. The identity and amount of the one or more polymers mixed into the aqueous foam as additives can be as discussed above regarding the provided compositions. For example, the additives can include between about 1 wt % and about 10 wt % of the polymers, and the polymers can include gelatin, chitosan, or a combination thereof. The identity and amount of the one or more calcium phosphate cements mixed into the aqueous foam as additives can be as discussed above regarding the provided compositions. For example, the additives can include between about 10 wt % and about 35 wt % of the calcium phosphate cements, and the calcium phosphate cements can include calcium-deficient hydroxyapatite, hydroxyapatite, brushite, or any combination thereof.

In some embodiments, the method further includes a step of curing the homogeneous paste to produce a cement. The conditions of the curing are generally sufficient to transform the homogenous paste to a cement having the advantageous characteristics disclosed herein. In some embodiments, the method further includes a step of selecting one or more conditions of the curing, such that the selections are sufficient to provide the cement with certain advantageous characteristics related to the porosity, mechanical strength, or crystal phase compositions disclosed herein.

A further benefit of the provided method is that the curing of the composition into a cement form can be easily accomplished at temperatures close to room temperature. The conditions of the curing can include a temperature that is, for example, between about 30° C. and about 40° C., e.g., between about 30° C. and about 36° C., between about 31° C. and about 37° C., between about 32° C. and about 38° C., between about 33° C. and about 39° C., or between about 34° C. and about 40° C. In terms of lower limits, the temperature of the curing can be, for example, at least about 30° C., e.g., at least about 31° C., at least about 32° C., at least about 33° C., at least about 34° C., at least about 35° C., at least about 36° C., at least about 37° C., at least about 38° C., or at least about 39° C. In terms of upper limits, the temperature of the curing can be, for example, at most about 40° C., e.g., at most about 39° C., at most about 38° C., at most about 37° C., at most about 36° C., at most about 35° C., at most about 34° C., at most about 33° C., at most about 32° C., or at most about 31° C. Higher temperatures, e.g., greater than about 40° C., and lower temperatures, e.g. less than about 30° C., are also contemplated.

The conditions of the curing can include a duration that is, for example, between about 24 hours and about 120 hours, e.g., between about 24 hours and about 82 hours, between about 34 hours and about 91 hours, between about 43 hours and about 100 hours, between about 53 hours and about 110 hours, or between about 62 hours and about 120 hours. In terms of lower limits, the duration of the curing can be, for example, at least about 24 hours, e.g., at least about 34 hours, at least about 43 hours, at least about 53 hours, at least about 62 hours, at least about 72 hours, at least about 82 hours, at least about 91 hours, at least about 100 hours, or at least about 110 hours. In terms of upper limits, the duration of the curing can be, for example, at most about 120 hours, e.g., at most about 110 hours, at most about 100 hours, at most about 91 hours, at most about 82 hours, at most about 72 hours, at most about 62 hours, at most about 53 hours, at most about 43 hours, or at most about 34 hours. Longer durations, e.g., more than about 120 hours, and shorter durations, e.g., less than about 24 hours, are also contemplated.

V. Methods for Repairing Bone Defects

Another aspect of the present disclosure relates to methods for repairing a bone defect in a subject. The particular features of the methods have been shown to provide a subject with treatments benefiting from the enhanced characteristics of the compositions and scaffolds disclosed herein. The methods generally include implanting a bone repair scaffold in a subject. The bone repair scaffold can be any of those discussed above. The bone repair scaffold can be implanted in the subject at a location proximate to a bone defect of the subject, e.g., at the site of the bone defect.

As used herein, the term "subject" refers to a vertebrate, and preferably to a mammal. Mammalian subjects for which the provided composition is suitable include, but are not limited to, mice, rats, simians, humans, farm animals, sport animals, and pets. In some embodiments, the subject is human. In some embodiments, the subject is male. In some embodiments, the subject is female. In some embodiments, the subject is an adult. In some embodiments, the subject is an adolescent. In some embodiments, the subject is a child. In some embodiments, the subject is above about 10 years of age, e.g., above about 20 years of age, above about 30 years of age, above about 40 years of age, above about 50 years of age, above about 60 years of age, above about 70 years of age, or above about 80 years of age. In some embodiments, the subject is less than about 80 years of age, e.g., less than about 70 years of age, less than about 60 years of age, less than about 50 years of age, less than about 40 years of age, less than about 30 years of age, less than about 20 years of age, or less than about 10 years of age.

In some embodiments, the method further includes introducing one or more types of cells to the bone repair scaffold. The adhering of the cells to the scaffold can include seeding cells onto the scaffold prior to or subsequent to implantation in a subject. In some embodiments, one or more cell types promoting bone repair are adhered to the scaffold. The cell types can be any of those disclosed herein. For example, the cells adhered to the scaffold can include mesenchymal stem cells, osteoblasts, fibroblasts, endothelial cells, or any combination thereof.

The bone defect of the subject can be the result of a cancer; a hereditary disease; age-related bone loss, e.g., osteoporosis; a trauma, e.g., an injury; or an infection. Accordingly, the provided bone repair scaffold can be implemented in treatments related to orthopedics, reconstructive surgery, dentistry, and podiatry. In some embodiments, the bone defect site includes a degenerated or damaged spinal disc, an oral defect, or a maxillofacial defect. Oral and maxillofacial defects that can be repaired with the provided bone repair scaffold include defects in the head, neck, face, and jaws regions. Exemplary bone defects include diseased, degenerated, missing, or damaged, e.g., broken fractured, or cracked, bones.

In some embodiments, the method further includes evaluating the subject to determine the nature of the bone defect that requires repair, and the characteristics of the bone repair scaffold appropriate to treat the subject. The evaluating of the subject can include medical imaging, such as X-ray imaging, MRI scans, or CT scans, which can provide dimensions of the bone defect site, and can be utilized for determining the desired configuration, such as size and/or shape, of the bone repair scaffold.

VI. Exemplary Embodiments

The following embodiments are contemplated. All combinations of features and embodiments are contemplated.

Embodiment 1: A composition comprising: 15 wt % to 70 wt % magnesium oxide; 2 wt % to 10 wt % magnesium chloride; 0.2 wt % to 2 wt % of a surface modifying agent; and 20 wt % to 65 wt % water; wherein the identity and amount of the surface modifying agent are effective to modify at least a portion of the magnesium oxide, thereby creating particulates sufficient for stabilizing a Pickering foam form of the composition.

Embodiment 2: An embodiment of embodiment 1, wherein the surface modifying agent is a short-chain amphiphilic compound.

Embodiment 3: An embodiment of embodiment 2, wherein the short-chain amphiphilic compound is propyl gallate, hexanoic acid, or gallic acid.

Embodiment 4: An embodiment of any of the embodiments of embodiment 1-3, wherein the molar ratio of the magnesium oxide to the magnesium chloride is between 2.5:1 and 15:1.

Embodiment 5: An embodiment of any of the embodiments of embodiment 1-4, wherein the molar ratio of the water to the magnesium chloride is between 5:1 and 25:1.

Embodiment 6: An embodiment of any of the embodiments of embodiment 1-5, comprising: 30 wt % to 60 wt % magnesium oxide; 4 wt % to 8 wt % magnesium chloride; 0.4 wt % to 1.3 wt % propyl gallate, hexanoic acid, or gallic acid; and 30 wt % to 55 wt % water.

Embodiment 7: An embodiment of any of the embodiments of embodiment 1-6, further comprising a soluble phosphate compound.

Embodiment 8: An embodiment of embodiment 7, wherein the soluble phosphate compound is phosphoric acid, sodium dihydrogen phosphate, or disodium hydrogen phosphate.

Embodiment 9: An embodiment of embodiment 7 or 8, wherein the concentration of the soluble phosphate compound in the composition is between 0.1 wt % and 2 wt %.

Embodiment 10: An embodiment of any of the embodiments of embodiment 1-9, further comprising gelatin or chitosan.

Embodiment 11: An embodiment of embodiment 10, wherein the concentration of the gelatin or chitosan in the composition is between 1 wt % and 10 wt %.

Embodiment 12: An embodiment of any of the embodiments of embodiment 1-11, further comprising a calcium phosphate cement, wherein the calcium phosphate cement is calcium-deficient hydroxyapatite, hydroxyapatite, or brushite.

Embodiment 13: An embodiment of embodiment 12, wherein the concentration of the calcium phosphate cement is between 10 wt % and 35 wt %.

Embodiment 14: An embodiment of any of the embodiments of embodiment 1-6, having the form of a Pickering foam.

Embodiment 15: An embodiment of any of the embodiments of embodiment 7-13, having the form of a homogeneous paste.

Embodiment 16: A cement, wherein the cement is formed by curing the homogeneous paste of embodiment 15, and wherein the cement comprises a plurality of pores.

Embodiment 17: An embodiment of embodiment 16, wherein at least 10% of the plurality of pores each independently has a diameter greater than 50 μm.

Embodiment 18: An embodiment of embodiment 16 or 17, wherein at least 90% of the plurality of pores each independently has a diameter greater than 10 μm.

Embodiment 19: An embodiment of any of the embodiments of embodiment 16-18, comprising $xMg(OH)_2 \cdot yMgCl_2 \cdot zH_2O$ crystals, wherein at least 70% of the $xMg(OH)_2 \cdot yMgCl_2 \cdot zH_2O$ crystals are phase 5 ($5Mg(OH)_2 \cdot MgCl_2 \cdot 8H_2O$) crystals.

Embodiment 20: A bone repair scaffold comprising the cement of any of the embodiments of embodiment 16-19.

Embodiment 21: An embodiment of embodiment 20, further comprising cells adhered to the cement, wherein the cells comprise mesenchymal stem cells, osteoblasts, fibroblasts, endothelial cells, or a combination thereof Embodiment 22: A method for producing a magnesium oxychloride cement, the method comprising: forming a mixture of magnesium oxide and a surface modifying agent dispersed in an aqueous magnesium chloride solution; and frothing the mixture under frothing conditions sufficient to generate an aqueous foam.

Embodiment 23: An embodiment of embodiment 22, wherein the aqueous foam is a Pickering foam.

Embodiment 24: An embodiment of embodiment 22 or 23, wherein the frothing conditions comprise a frothing agitation rate between 6000 rpm and 20,000 rpm.

Embodiment 25: An embodiment of any of the embodiments of embodiment 22-24, wherein the frothing conditions comprise a frothing duration between 10 seconds and 60 seconds.

Embodiment 26: An embodiment of any of the embodiments of embodiment 22-25, wherein the mixture comprises 15 wt % to 70 wt % magnesium oxide.

Embodiment 27: An embodiment of any of the embodiments of embodiment 22-26, wherein the mixture comprises 2 wt % to 10 wt % magnesium chloride.

Embodiment 28: An embodiment of any of the embodiments of embodiment 22-27, wherein the mixture comprises 0.2% to 2 wt % of the surface modifying agent.

Embodiment 29: An embodiment of any of the embodiments of embodiment 22-28, wherein the surface modifying agent is a short-chain amphiphilic compound.

Embodiment 30: An embodiment of embodiment 29, wherein the short-chain amphiphilic compound is propyl gallate, hexanoic acid, or gallic acid.

Embodiment 31: An embodiment of any of the embodiments of embodiment 22-30, further comprising: mixing one or more additives into the aqueous foam under conditions sufficient to produce a homogenous paste, wherein the one or more additives are selected from the group consisting of a soluble phosphate compound, gelatin, chitosan, a calcium phosphate cement, and additional magnesium oxide.

Embodiment 32: An embodiment of embodiment 31, wherein homogeneous paste comprises a soluble phosphate, gelatin or chitosan, and a calcium phosphate cement.

Embodiment 33: An embodiment of embodiment 31 or 32, wherein the concentration of the soluble phosphate compound in the homogenous paste is between 0.2 wt % and 2 wt %.

Embodiment 34: An embodiment of any of the embodiments of embodiment 31-33, wherein the concentration of the gelatin or chitosan in the homogeneous paste is between 1 wt % and 10 wt %.

Embodiment 35: An embodiment of any of the embodiments of embodiment 31-34, wherein the concentration of the calcium phosphate cement in the homogeneous paste is between 10 wt % and 35 wt %.

Embodiment 36: An embodiment of any of the embodiments of embodiment 31-35, further comprising: curing the homogenous paste under curing conditions sufficient to produce the magnesium oxychloride cement.

Embodiment 37: An embodiment of embodiment 36, wherein the curing conditions comprise a curing temperature between 30° C. and 40° C.

Embodiment 38: An embodiment of embodiment 36 or 37, wherein the curing conditions comprise a curing duration between 24 hours and 120 hours.

Embodiment 39: A method for repairing a bone defect in a subject, the method comprising implanting the bone repair scaffold of embodiment 20 or 21 in the subject proximate to the bone defect.

EXAMPLES

The present disclosure will be better understood in view of the following non-limiting examples. The following examples are intended for illustrative purposes only and do not limit in any way the scope of the present invention

Example 1. Fabrication of Calcium Deficient Hydroxyapatite (CDHA)

CDHA paste was prepared by directly mixing α-tricalcium phosphate (α-TCP) and 2.5 wt % $Na_2HPO_4$ aqueous solution at a ratio of 3 g/mL. The CDHA paste was then transferred to specific polytetrafluoroethylene (PTFE) molds, sealed, and incubated for 3 days at 37° C. and 100% humidity to allow absolute curation.

Figure 2:
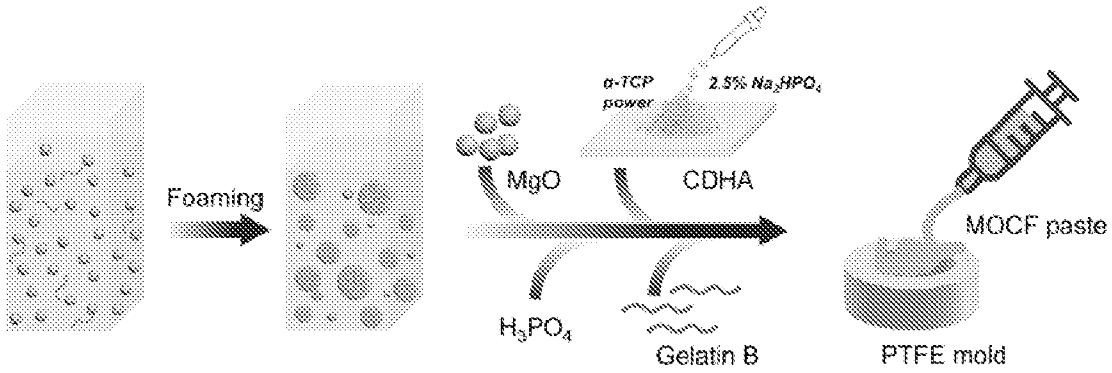
FIG. 2 is a schematic illustration of the fabrication of an MOCF paste in accordance with a provided embodiment.
Figure 7:
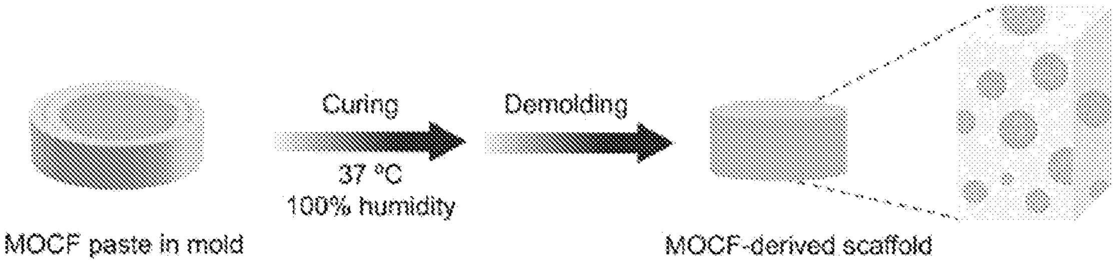
FIG. 7 is a schematic illustration of the fabrication of an MOCF-derived scaffold in accordance with a provided embodiment via the curation of MOCF paste in a mold.

Example 2. Fabrication of Magnesium Oxychloride Cement (MOC) foam (MOCF)-Derived Scaffold The MOCF-derived scaffold was fabricated according to the formulation shown in Table 1, based on the Pickering foaming technique (FIG. 2). In an exemplary procedure, 0.9 g MgO microparticles and 0.03 g propyl gallate were dispersed into 1.4 g $MgCl_2$ solution, which was immediately frothed by homogenization for 30 s at 8000 rpm to generate an aqueous foam. Afterward, another 0.6 g MgO microparticles was added to the obtained foam, followed by the addition of 0.5 wt % $H_3PO_4$, 3.5 wt % Gelatin B (from bovine skin, ~225 bloom), and the as-prepared CDHA paste (Example 1) at the prescribed concentration. The resulting combination was mixed gently using a stirring rod to generate a homogeneous MOCF paste (FIG. 2). The MOCF pastes were then transferred to specific PTFE molds, sealed, and incubated at 37° C. and 100% humidity to allow curing for 3 days (FIG. 7).

TABLE 1

Formulation for the fabrication of MOCF-derived scaffold.

| $MgO/MgCl_2/H_2O$ | Foaming conditions | Additives |
|---|---|---|
| 8.5:1:16 (molar ratio) | 0.6 wt % propyl gallate | 0.5 wt % $H_3PO_4$ |
| | 8000 rpm | 3.5 wt % Gelatin B |
| | 30 s | CDHA (α-TCP/MgO = 0.5, molar ratio) |

Example 3. Evaluation of the Handling Performance of the MOCF-Derived Scaffold The injectability of the as-prepared MOCF paste of Example 2 was examined using a 5-mL syringe. Briefly, the MOCF paste was prepared and immediately extruded from the syringe via a material test system (QTest, Artisan Technology Group, USA) at a speed of 15 mm/min until reaching the maximum force of 200 N. The extrusion curve (force versus syringe plunger displacement) was recorded. The mass of the extruded paste was weighed, and the percentage of the extruded paste was calculated accordingly. To evaluate the cohesion performance, the newly prepared MOCF paste was directly injected into phosphate buffered saline (PBS) at 37° C. and the behavior of the paste was observed during hardening. The setting process of the MOCF paste was monitored using a rheometer (Malvern Kinexus Lap+, Malvern Instrument Inc., UK) in a 20 mm-diameter parallel-plate geometry. The newly prepared MOCF paste was loaded into the gap of a 20 mm plate and underwent an oscillation time sweep rheological testing. The gap size, strain, and frequency were fixed at 1.5 mm, 1%, and 1 Hz, respectively. The elastic modulus (G'), viscous modulus (G") and viscosity (n) were recorded during measurements and plotted against time (t) to reveal the in-situ setting process of the MOCF paste.

Figure 3:
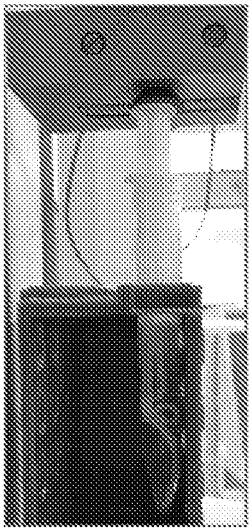
FIG. 3 is a photograph taken during measurement of the injectability of the MOCF paste.
Figure 4:
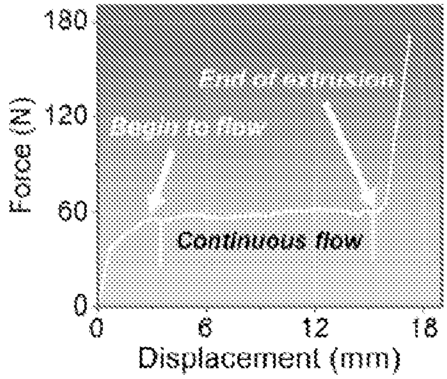
FIG. 4 is a graph plotting an extrusion curve recorded during the injection of the as-prepared MOCF paste via a 5-mL syringe.

Results from these investigations demonstrated that the provided MOCF scaffold presented a good handling performance in its paste state, which can therefore be adapted for minimally invasive surgery as an injectable scaffold. The fresh MOCF paste can be directly extruded out through a syringe immediately after the preparation with the extrusion rate of over 99 wt % (FIG. 3), suggesting the satisfactory injectability. The extrusion curve recorded during injection revealed the extrusion process of the MOCF paste in detail (FIG. 4). The overshot of the curve signifies the critical force to allow the paste flowing, and the plateau corresponded to the load (~60 N) required to maintain a homogeneous paste flow. The intensive increase of the force suggested the end of the extrusion, which could be attributed to the mechanical contact between the plunger and syringe bottom.

Figure 5:
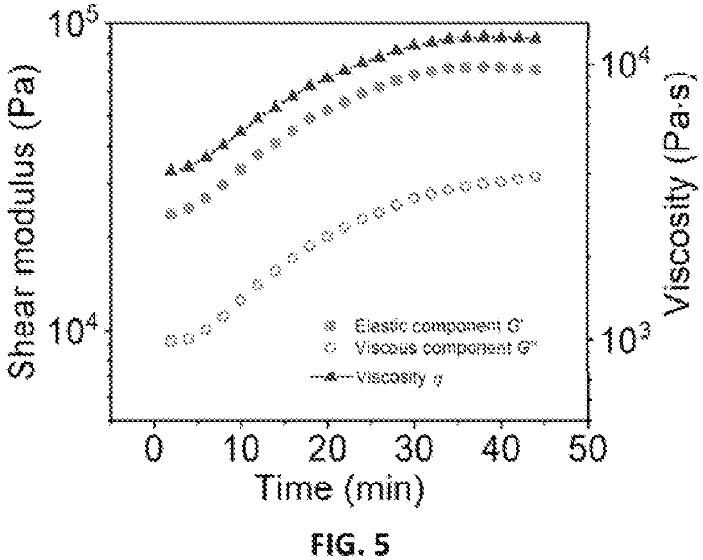
FIG. 5 is a graph plotting evolution curves of the elastic modulus, viscous modulus, and viscosity obtained from rheological measurements of the MOCF paste during curation.

The setting kinetic of MOCF paste was determined through dynamic rheological measurements. The elastic modulus (G') was shown to be always larger than the viscous modulus (G"), with both G' and G" increasing over time, validating the predominant solid-like characteristic of the paste (FIG. 5). The G' and G" curves gradually reached a plateau after around 35 min during the measurement. Such a plateau was also seen in the evolution of the viscosity ($\eta$), corresponding to the initial setting time point.

Figure 6:
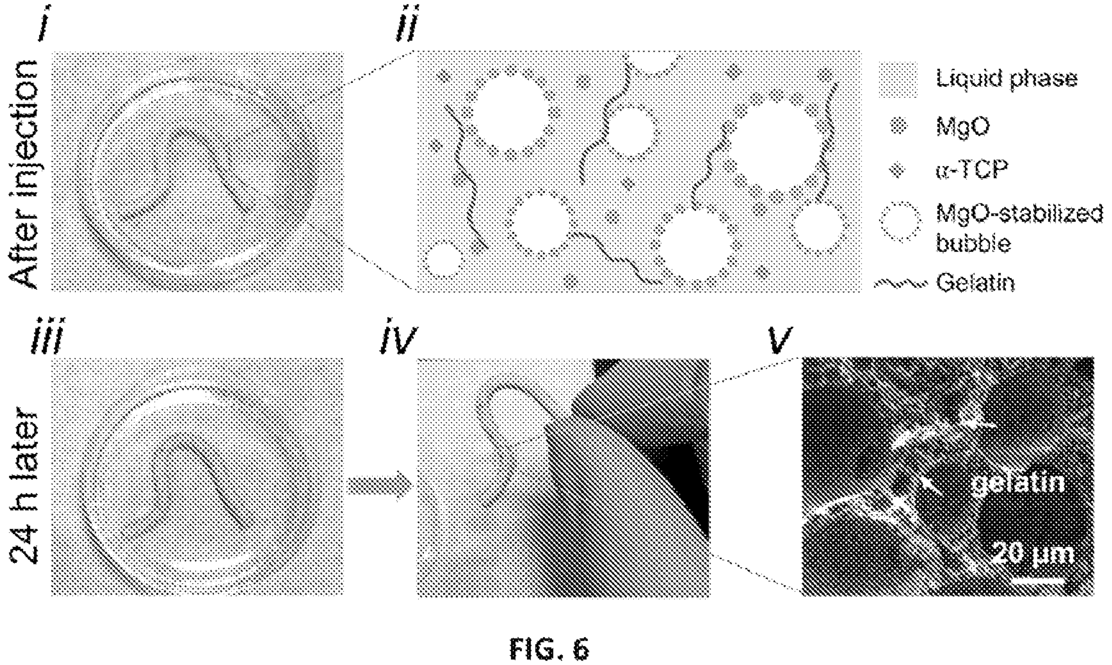
FIG. 6 presents a series of images demonstrating the cohesion performance of the MOC paste: (i) photograph of the MOCF paste after injection into a phosphate buffered saline (PBS) solution; (ii) schematic illustration of the constituents of the MOCF paste; (iii-iv) photographs of the MOCF paste after being cured for 24 h in PBS solution; (v) scanning electron microscopy (SEM) image of the intersectional morphology of the cured MOCF.

After injection into the PBS, the noodle-like MOCF paste could maintain its shape well, without any particle liberation, indicating superior cohesion performance (FIG. 6(*i*)). Such cohesiveness can be attributed to the presence of the tiny amount of gelatin. Without being bound by a particular theory, the inventors believe that the gelatin polymer chain serves as a "glue" to crosslink the inorganic species within the paste as illustrated by FIG. 6(*ii*). The paste can remain intact after 24 h whilst completing the curation (FIGS. 6(*iii*)-(iv)). The intersectional SEM image of the cured specimen also showed the deposition of the gelatin polymer on the cell wall (FIG. 6(*v*)).

Example 4. Characterization of Porosity Within the MOCF-Derived Scaffold

The intersectional morphologies of the cured CDHA and MOCF scaffolds of Example 1 and Example 2 were observed using scanning electron microscopy (SEM, Quanta-400, FEI, USA) at an accelerating voltage of 10 kV, after being sputtered with Au nanoparticles. The intersectional areas were created by cutting the samples with a scissor. Pore size distribution of the MOCF scaffold was analyzed with SEM and ImageJ software (version 1.52k).

Figure 8:
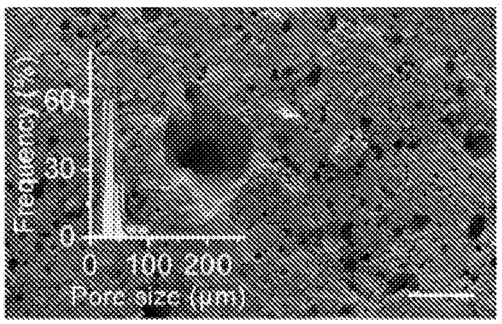
FIG. 8 presents an SEM image of intersectional morphologies of an MOCF-derived scaffold, and a graph plotting the pore size distribution of the MOCF scaffold.
Figure 9:
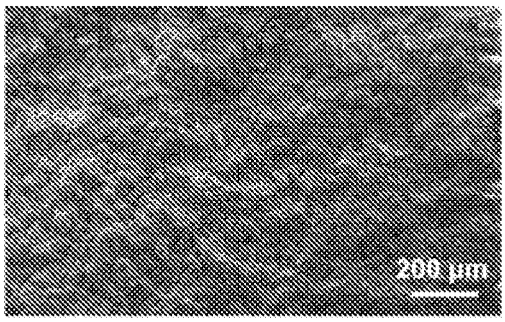
FIG. 9 is an SEM image of intersectional morphologies of a calcium deficient hydroxyapatite (CDHA) cement.

Results from these investigations showed that hierarchical porosity that could allow favorable osseointegration during implantation is generated within the MOCF scaffold after the absolute in-situ curing. After absolutely curing in molds, the solidified bulk could be obtained in a specific shape (FIG. 7). The hierarchical porous structure was constructed in MOCF scaffold, where the pore size ranged from tens of microns to over 100 microns (FIG. 8). Since the additives were introduced after the foaming step, and the mixture then underwent a mechanical stirring (FIG. 2), the pores in MOCF turned out to be distorted circular-shaped. In contrast, the traditional CDHA exhibited a dense and non-porous structure, with only nano-pores generated during cement formation (FIG. 9). In view of the needs of osseointegration, the porous MOCF scaffold should show superiority to the dense CDHA in its ability to guide cell and tissue ingress.

Example 5. Characterization of Crystal Formation Within the MOCF-Derived Scaffold Crystal phase analysis of the CDHA and MOCF samples from Example 1 and Example 2 was performed via X-ray diffraction (XRD, SmartLab, Rigaku, Japan) with the scanning range from 10° to 65° . Of the phases resulting from the aqueous reaction between MgO particles and an aqueous $MgCl_2$ solution, for the $MgO$—$MgCl_2$—$H_2O$ ternary system only the phase 3 ($3Mg(OH)_2 \cdot MgCl_2 \cdot 8H_2O$) and phase 5 ($5Mg(OH)_2 \cdot MgCl_2 \cdot 8H_2O$) exist at ambient temperature. It is widely accepted that the phase 5 crystal makes the major contribution to the mechanical integrity of the bulk MOC. Phase 5 crystals are therefore desired as the predominant phase for a MOC product having good mechanical properties.

Figure 10:
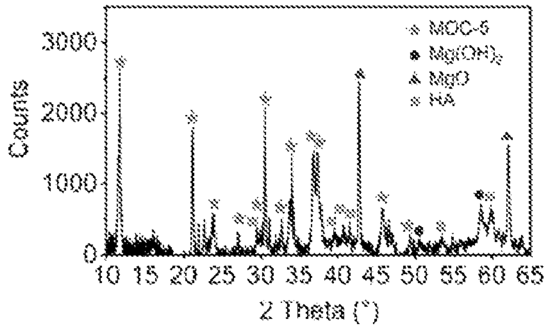
FIG. 10 is a graph showing the crystal phase composition of an MOCF-derived scaffold
Figure 11:
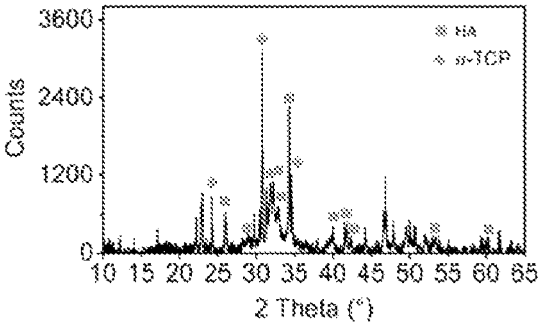
FIG. 11 is a graph showing the crystal phase composition of a CDHA cement.

The observations from the crystal phase analysis of the Example 2 MOCF samples showed that the provided formulation ensures the maximum phase 5 MOC crystal formation in the resulting MOCF scaffold. The XRD pattern demonstrated the predominance of crystalline phase 5 (MOC-5) in the MOCF scaffold, with only a small proportion of $Mg(OH)_2$ detected (FIG. 10). Some residual MgO could also be found in the product, likely due to the excess fed ratio. In addition, several small observed peaks were attributed to hydroxyapatite (HA), which was contributed by the incorporated CDHA. As shown in FIG. 11, HA was the predominant phase in CDHA cement, along with a small amount of the unreacted $\alpha$-tricalcium phosphate ($\alpha$-TCP).

Example 6. Evaluation of Mechanical Properties of the MOCF-Derived Scaffold

The mechanical performance of samples was evaluated through compression tests. Cylindrical MOCF and CDHA specimens ($\Phi$: 6 mm, l: 12 mm) were prepared and cured for 3 days at 37° C. and 100% humidity. The samples were then processed to compression testing at a loading rate of 1 mm/min using a universal testing machine (Instron, USA). The compressive strength and Young's modulus were then calculated from the strain-stress curves. The mechanical properties of MOCF and CDHA scaffolds after immersion in PBS (pH 7.40) for 8 weeks were also measured by the same protocol. Three specimens were measured for each sample.

Figure 12:
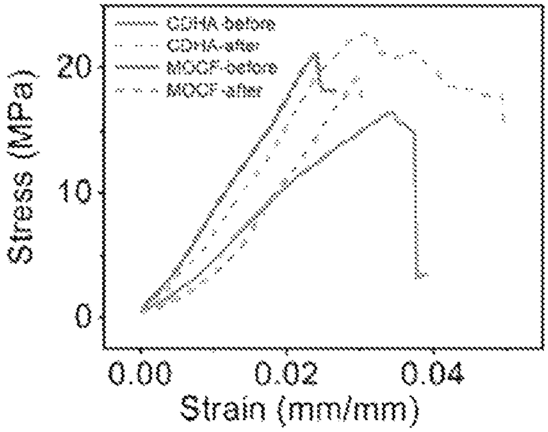
FIG. 12 is a graph plotting representative strain-stress curves obtained from compression tests of MOCF and CDHA before and after an 8-week immersion in PBS.
Figure 13:
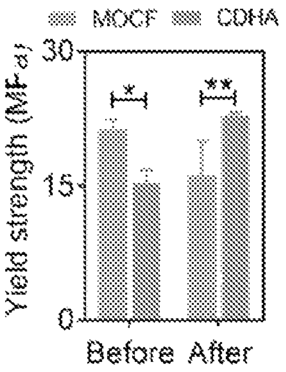
FIG. 13 is a graph plotting the yield strength of MOCF and CDHA as calculated from strain-stress curves before and after an 8-week immersion in PBS (n=3). Quantitative data are presented as mean±SD. Two-way ANOVA with Sidak's post hoc test was used. $*P<0.05$, $**P<0.01$.
Figure 14:
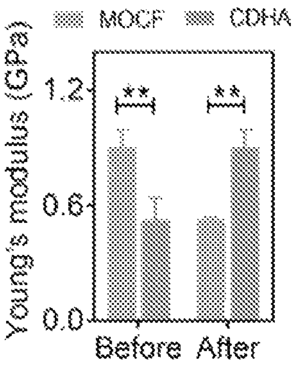
FIG. 14 is a graph plotting the Young's modulus of MOCF and CDHA as calculated from strain-stress curves before and after an 8-week immersion in PBS (n=3). Quantitative data are presented as mean±SD. Two-way ANOVA with Sidak's post hoc test was used. $**P<0.01$.

The results from these investigations indicated that the provided MOCF scaffold exhibited mechanical performance superior to that of traditional CDHA cement. The mechanical characterizations revealed a brittle fracture feature of the two scaffolds (FIG. 12). Both the yield strength and compressive modulus of MOCF (~21.31 MPa; ~0.90 GPa) were significantly higher than those of CDHA (~15.31 MPa; ~0.53 GPa) after setting for 3 days (FIGS. 13 and 14).

Example 7. Evaluation of Biodegradation Properties of the MOCF-Derived Scaffold

The degradation behaviors of MOCF and CDHA scaffolds were examined by immersing accurately weighed specimens ($\Phi$: 6 mm, l: 12 mm) in PBS (pH 7.40) at a weight-to-volume ratio of 0.2 g/mL at 37° C., under continuous shaking at 100 rpm. The soaking solutions were refreshed every 7 days (n=3). During the immersion process, the pH evolution and the concentration of ions ($Mg^{2+}$ and $Ca^{2+}$) in the soaking solutions were monitored at day 1, 3, 5, and 7. At the prescribed time points, 300 μL soaking solution was quantitatively extracted, with the subsequent addition of 300 μL fresh PBS solution to keep a constant volume. The pH value was measured using a pH meter (Sartorius, Germany), and the ion concentration was determined by an Inductively Coupled Plasma-Optical Emission Spectrometer (ICP-OES, ICPE-9820, Shimadzu, Japan). After immersion for 1, 2, 3, and 4 weeks, the specimens were removed from the soaking solutions, rinsed with deionized water, and dried at 37° C. The weight loss ratios of the specimens were measured and calculated as the percentage of the initial weight until a constant weight was achieved. Afterwards, the specimens were re-immersed into PBS with the same weight-to-volume ratio at 37° C. under continuous shaking. The crystal phase compositions of the samples after 4-week degradation were analyzed using XRD (SmartLab, Rigaku, Japan).

Figure 15:
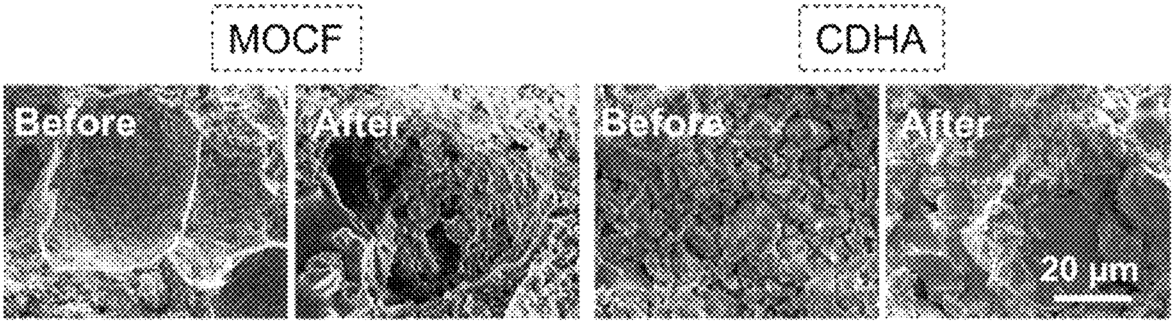
FIG. 15 presents SEM images showing intersectional morphological analyses of MOCF and CDHA samples before and after an 8-week immersion in PBS.

Reassessing the mechanical performance of the two scaffolds after an 8-week immersion in PBS solution showed that the inner structure and mechanical strength of MOCF were deteriorated (FIGS. 12-15). For example, the pore wall in MOCF could be penetrated by corrosive fluid (FIG. 15). In contrast, CDHA was mechanically strengthened relative to MOCF following the prolonged immersion, with the compressive strength and modulus of CDHA (~22.91 MPa; ~0.71 GPA) becoming significantly higher than those of MOCF (~16.17 MPa; ~0.53 GPa). This increase in mechanical strength seen with the CDHA material was likely attributable to the larger bulks formed in CDHA after the immersion (FIG. 15). Overall, the mechanical properties of either MOCF or CDHA before and after immersion could match those of cancellous bone, allowing them to hold the structure of tissue layer during vascularization and bony regeneration.

Figure 16:
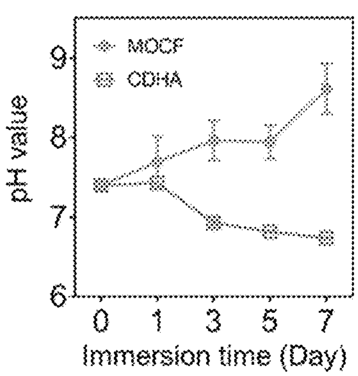
FIG. 16 is a graph plotting the pH evolution of a PBS soaking solution for MOCF and CDHA during the first week of a 4-week degradation test (n=3). Quantitative data are presented as mean±SD.
Figure 17:
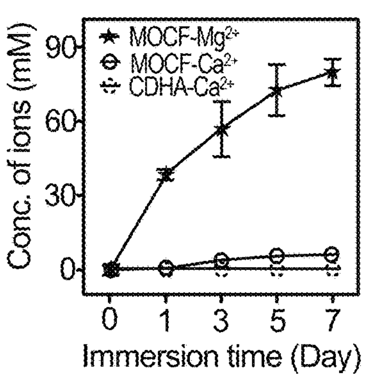
FIG. 17 is a graph plotting the concentrations of released ions (i.e., Mg2+ and $Ca^{2+}$) in a PBS soaking solution for MOCF and CDHA during the first week of a 4-week degradation test (n=3).
Figure 19:
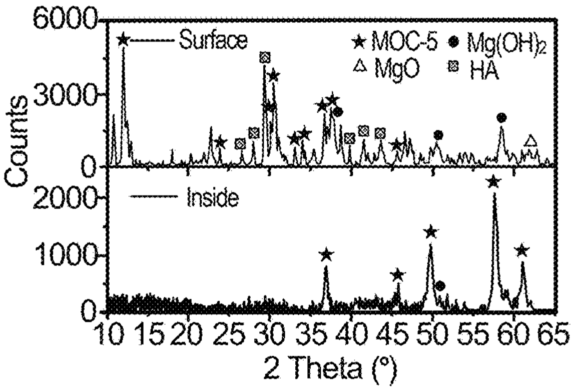
FIG. 19 is a graph showing the crystal phase composition of the surface and inside of MOCF after soaking in a PBS solution during a 4-week degradation test.

For the MOCF samples, a clear alkaline shift could be found, and the pH value of soaking solution would reach 8.65 after 7 days, which was related to the phase transition and dissolution of phase 5 crystals (FIGS. 16 and 19). Upon exposure to an aqueous environment, the phase 5 compound gradually transited to the slight-soluble $Mg(OH)_2$, which then further transformed into water-soluble $MgCl_2$ in the presence of relatively high-concentrations of Cl and released hydroxyl ions (OH), thus inducing the pH increase. In the meanwhile, the concentration level of $Mg^{2+}$ became elevated as a result of the dissociation of $MgCl_2$, with the cumulative level reaching ~79.6 mM after 1 week (FIG. 17). Additionally, approximately 6 mM calcium ions ($Ca^{2+}$) were released within the first week, with contributions from the incorporated small proportion of CDHA.

Figure 18:
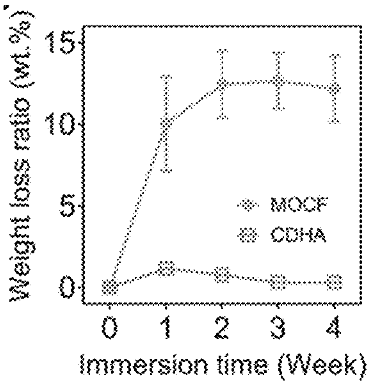
FIG. 18 is a graph plotting weight loss curves for MOCF and CDHA specimens after soaking in a PBS solution during a 4-week degradation test (n=3). Quantitative data are presented as mean±SD.
Figure 20:
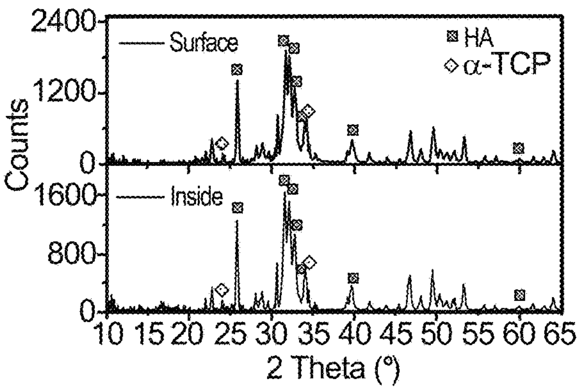
FIG. 20 is a graph showing the crystal phase composition of the surface and inside of CDHA after soaking in a PBS solution during a 4-week degradation test.

In contrast, there was a slight acidic shift for the CDHA samples, for which the pH value became lower than 7.00 after 1 week (FIG. 16). Almost no ion release could be detected during the immersion. This finding, along with the quite low weight loss ratio, demonstrated the inferior degradability of the relatively non-porous CDHA. Rather, an increase in weight could be found in CDHA after immersion for 2 weeks (FIGS. 17 and 18), with the gain possibly caused by the reprecipitation of HA on the sample surfaces (FIG. 20). HA formation also appeared on the MOCF surface (FIG. 19), and such surface-deposited HA would impede the degradation process, as seen in the gradual formation of a plateau (reached about 13 wt % after 4 weeks) in the weight loss curve of MOCF (FIG. 18).

These results revealed the more beneficial degradation kinetics of the provided MOCF scaffold relative to the CDHA cement. The advantageous characteristics are due to the better water-solubility of MOC and the introduction of micro- and macro-porosity through features particular to the materials and methods disclosed herein. The desirable in vitro degradation behavior can simulate the in vivo resorption process to a certain extent, suggesting a favorable resorption rate capable of achieving the total replacement of implanted MOCF by regenerated bone tissue.

Example 8. Cell Integration Behaviors of the MOCF-Derived Scaffold

Cell adhesion and attachment on MOCF and CDHA scaffolds were observed via SEM imaging (Quanta-400, FEI, USA). $1.5\times10^5$ cells were seeded on the sterilized samples (Φ: 8 mm, l: 2 mm) in a 6-well plate, followed by incubation for 1 and 5 days under cell culture conditions. At the prescribed time points, samples were rinsed with PBS (pH 7.40) to remove any non-adherent cells or impurities. The cells adhered to the samples were then fixed with 2.5% glutaraldehyde (Sigma) in PBS (10×, pH 7.40) overnight at 4° C. After fixation, the samples were washed with PBS (10×, pH 7.40) for 3 times to remove the residual crosslinking agent, and then subjected to gradient dehydration with a series of 30, 50, 70, 90, 95, and 100 vol. % ethanol, at a period of 5 min each. Finally, the samples were soaked in hexamethyldisilazane (HMDS, Sigma) for 15 min, and subsequently air-dried overnight. The samples were then imaged through SEM (Quanta-400, FEI, USA) at 10 kV after being sputtered with Au nanoparticles. Cell spreading areas were measured with SEM and ImageJ software (version 1.52k).

Figure 21:
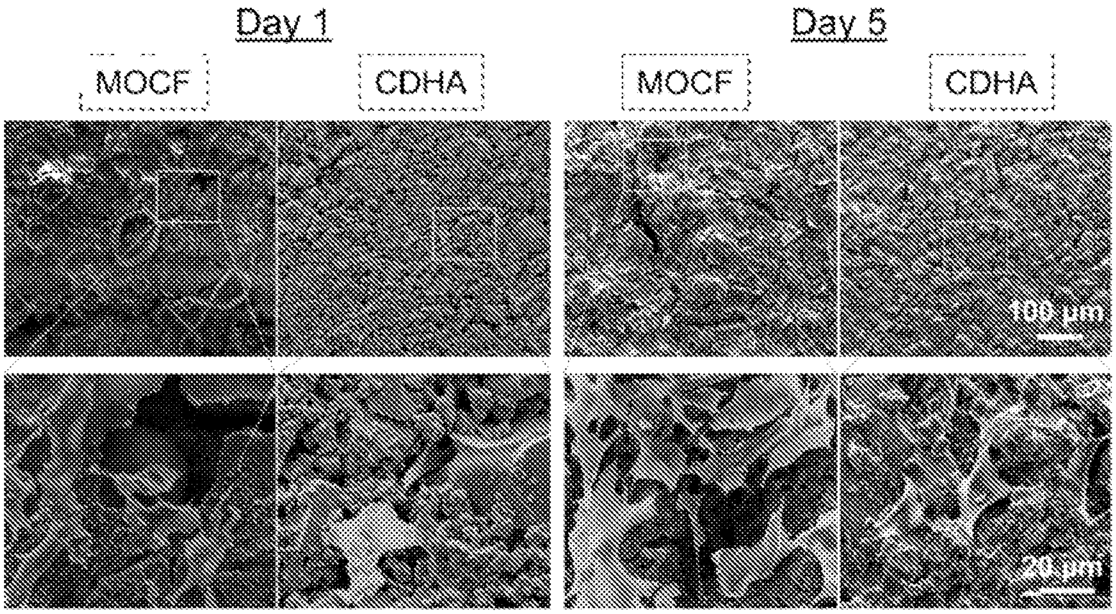
FIG. 21 presents representative SEM images of MC3T3-E1 preosteoblastic cells cultured on MOCF and CDHA scaffolds for 1 and 5 days.
Figure 22:
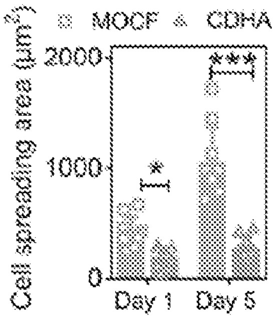
FIG. 22 is a graph plotting spreading areas of MC3T3-E1 cells cultured on MOCF and CDHA scaffolds for 1 and 5 days (n=8). Quantitative data are presented as mean±SD. *P<0.05, P<0.01, *P<0.001. Two-way ANOVA with Sidak's post hoc test was used.

Only a limited number of cells could grow on CDHA surface (FIG. 21). Further, although cells could adhere to the CDHA surface with their pseudopod-like protrusions anchoring to the surface cracks, the CDHA-adhered cells displayed remarkably lower spreading areas than those adhered to MOCF surface (FIGS. 21 and 22). The MC3T3-E1 preosteoblasts could attach well to the MOCF surface, with the cells exhibiting a polygonal shape with their stretching filopodia and lamellipodia. Moreover, the MOCF-adhered cells showed clear ingress into the pores of the scaffold at day 1 post-seeding. After 5 days, there was a considerable increase in cell density with nearly the whole MOCF surface covered by cells. These observations revealed an outstanding cell proliferation capacity for the provided MOCF scaffold (FIG. 21). The hierarchical porous MOCF scaffold can better support osteoblastic cell attachment, infiltration, and proliferation than the non-porous CDHA, and can accordingly dramatically improve cell-material integration.

Example 9. In vitro Osteogenic Differentiation Associated with the MOCF-Derived Scaffold Osteogenic differentiation of rat bone marrow mesenchymal stem cells (rBMSCs) on the prepared MOCF and CDHA scaffolds was evaluated via an indirect contact method using sample extracts. rBMSCs were isolated from the bone marrow of 6-week-old Sprague Dawley (SD) rats. Cells at passage 2 were used in this experiment. Sample extracts (0.2 g/mL) were collected by immersing specimens in osteogenic induction medium (OIM, cell culture medium supplemented with 10 mM β-glycerol phosphate (Sigma), 10 nM dexamethasone (Sigma) and 75 μM L-ascorbic acid (Sigma)) for 24 h, and extracts at dilution rates of 5 (1:5) and 10 (1:10) were utilized for testing.

In brief, rBMSCs were seeded in 24-well plate at a concentration of $3\times10^4$ cells/well and cultured for 2 days to allow for optimal attachment. The cell culture media were then replaced by the sample extracts for further induction, with OIM applied to a control group. The sample extracts and OIM were refreshed every 2 days. After induction for 10 days, ARS (Beyotime) staining was performed according to the manufacturer's instructions, and stained samples were digitalized using a biological scanner (Epson, Japan).

The osteogenic differentiation of rBMSCs was further assessed by quantitative real-time polymerase chain reaction (RT-qPCR) to detect the expression of osteogenesis-related genes including osteopontin (Opn), runt-related transcription factor 2 (Runx2), and osterix (Sp7). rBMSCs were seeded in a 6-well plate at a concentration of $2\times10^5$ cells/well and cultured for 2 days to allow for full attachment. The cell culture media were then replaced by the sample extracts (1:10) for further induction, with OIM applied to a control group. The sample extracts and OIM were refreshed every 2 days. After induction for 3 and 10 days, the total RNA was extracted from the cells using TRIzol reagent (Invitrogen). The extracted RNA was quantified using an ND-2000 spectrophotometer (NanoDrop Technologies, Wilmington, DE, USA). Equal quantities (500 ng) of total RNA from each sample were reverse-transcribed to cDNA using a cDNA kit (Takara). The cDNA was then amplified with SYBR Green qPCR SuperMix-UDG (Takara) and specific primer sequences (Table 2). The qRT-PCRs were run on a QuantStudio™ 12K Flex Real-time PCR system (Life Technologies, Thermo Fisher Scientific, USA).

TABLE 2

Primer sequences utilized for RT-qPCR.

| Gene | Oligonucleotide primer |
|---|---|
| Opn-F | AGCAAGAAACTCTTCCAAGCAA |
| Opn-R | GTGAGATTCGTCAGATTCATCCG |
| Sp7-F | GAGCAAACATCAGCGCACC |
| Sp7-R | GCGGCTGATTGGCTTCTTCTTC |
| Runx2-F | GCCTTCAAGGTTGTAGCCCT |
| Runx2-R | TGAACCTGGCCACTTGGTTT |
| Gapdh-F | CATGGCCTTCCGTGTTCCTA |
| Gapdh-R | CCTGCTTCACCACCTTCTTGAT |

Figure 23:
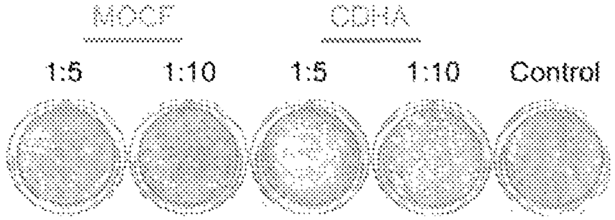
FIG. 23 presents representative images of Alizarin Red S (ARS) staining of MOCF and CDHA scaffolds after a 10-day osteogenic induction of rat bone marrow mesenchymal stem cells (rBMSCs).

Mineral deposition is a key late-stage marker of osteogenic differentiation. Through Alizarin Red S (ARS) staining, deposited calcium nodules were stained in red (FIG. 23). The MOCF group presented the most intense red color and calcium nodules formation, especially for the 1:10 extract, in comparison with the CDHA or control group, suggesting promoted osteogenesis of the rBMSCs. In contrast, the CDHA extracts showed a suppressive effect on the osteogenesis of rBMSCs, where only pale red staining could be observed (FIG. 23).

Figure 24:
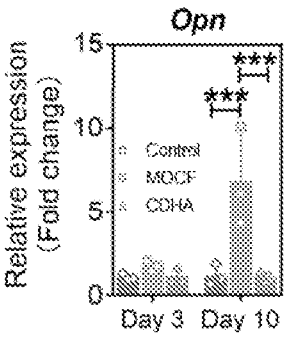
FIG. 24 is a graph plotting the relative expression of Opn in rBMSCs after osteogenic induction for 3 and 10 days (n=3), revealing in vitro osteogenic differentiation of the cells after incubation in the sample extracts of MOCF and CDHA. Quantitative data are presented as mean±SD. ***P<0.001. Two-way ANOVA with Sidak's post hoc test was used.
Figure 25:
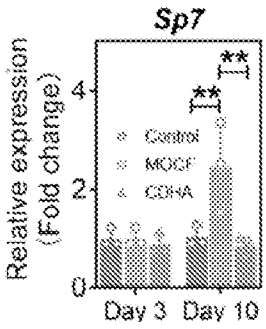
FIG. 25 is a graph plotting the relative expression of Sp7 in rBMSCs after osteogenic induction for 3 and 10 days (n=3), revealing in vitro osteogenic differentiation of the cells after incubation in the sample extracts of MOCF and CDHA. Quantitative data are presented as mean±SD. **P<0.01. Two-way ANOVA with Sidak's post hoc test was used.
Figure 26:
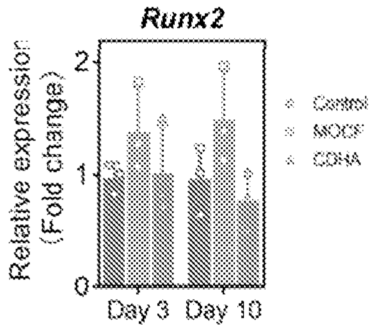
FIG. 26 is a graph plotting the relative expression of Runx2 in rBMSCs after osteogenic induction for 3 and 10 days (n=3), revealing in vitro osteogenic differentiation of the cells after incubation in the sample extracts of MOCF and CDHA. Quantitative data are presented as mean±SD. Two-way ANOVA with Sidak's post hoc test was used.

The relative expression of the osteogenic genes, Sp7, Runx2, and Opn, was then analyzed in the rBMSCs to further determine the osteo-promotive effect of the MOCF scaffold. After induction for 3 days, there was no significant difference in the expression levels of the three examined markers among the three groups, even if the rBMSCs in MOCF group showed the higher expression of Opn and Runx2 than the other two groups (FIGS. 24-26). The expression levels of Opn and Sp7, however became remarkably unregulated in MOCF group after a 10-day induction, such that the levels were significantly higher than those for the CDHA or control group (FIGS. 24 and 25). These results suggest a better performance of the MOCF scaffolds in enhancing osteogenic differentiation compared to CDHA. The MOCF degradation can contribute to an inductive microenvironment (containing the osteoinductive $Mg^{2+}$), which should be beneficial for eliciting desirable osteogenesis.

Example 10. In vivo Application of the MOCF-Derived Scaffold for Rat Osteoporotic Femoral Defect Repair The in vivo efficacy of the provided MOCF-derived scaffold was further assessed in a femoral defect model of osteoporotic rat, where the traditional CDHA was applied as the comparison group. Twelve-week-old female SD rats first received an ovariectomy (OVX) surgery. The OVX surgery was performed with anesthesia by intraperitoneally (i.p.) injection of a mixture of xylazine, ketamine, and saline with a volume ratio of 2:3:3 at a dose of 2 ml/kg body weight. Briefly, the abdominal cavity was accessed by a 10 mm midline dorsal incision after hair shaving, which allowed for the retraction of abdominal organs outside of the abdomen with sterile gauze to expose the ovaries. The ovaries were cut and removed with two ligatures. After 12 weeks, the OVX rats were used to establish a femoral defect model. The animal study was divided into two groups: MOCF and CDHA (n=6). After deep anesthesia, the left medial side of the distal femur was exposed. A tunnel bone defect, 2 mm in diameter and 8 mm in length, was created perpendicular through the bone surface by an orthopedic drill with constant saline cooling. Rats were randomly implanted with cylindrical CDHA or MOCF scaffolds (Φ:2 mm, l: 8 mm) into defects. All abdominal muscle was entirely closed in two layers with absorbable sutures, and skin was then closed with non-resorbable sutures. TEMGESIC™ (0.05 mg/kg) was administered to the rats once daily for 3 days to minimize pain suffered after surgery. All rats were housed under a 12-hour light/dark cycle, an ambient temperature of 18-23° C., and 68% humidity at the Experimental Animal Center at the Prince of Wales Hospital in Hong Kong and received food and water. All animal experimental protocols were approved by the Animal Experiment Ethics Committee of the Chinese University of Hong Kong.

At weeks 4 and 12 post operation, the femoral samples were harvested for X-ray and micro computed tomography (micro-CT) analysis. The femora were subjected to radiographic imaging (The XPERT 80 Cabinet X-ray System, KUBTEC, USA) by placing in the sagittal and coronal plane respectively with an exposure of 30 kV and 700 μA for seconds. After fixation, the femora were fitted in a sample tube (Ø: 30 mm) and scanned with a μCT-40 imaging system (μCT40, Scanco Medical, Brttittisellen, Switzerland). An analyzed length of about 1.5 mm (100 slides) was used to obtain information related to newly formed trabecular bone within the defects excluding the bone cements. To define mineralized tissue, background noise was removed using a low-pass Gaussian filter (Sigma=0.8, Support=1) with mineralized tissue being defined at a threshold of 210. The information obtained with the analysis included data for bone mineral density (BMD), bone volume fraction (BV/TV), trabecular number (Tb.N), and trabecular bone separation (Tb.Sp).

Figure 27:
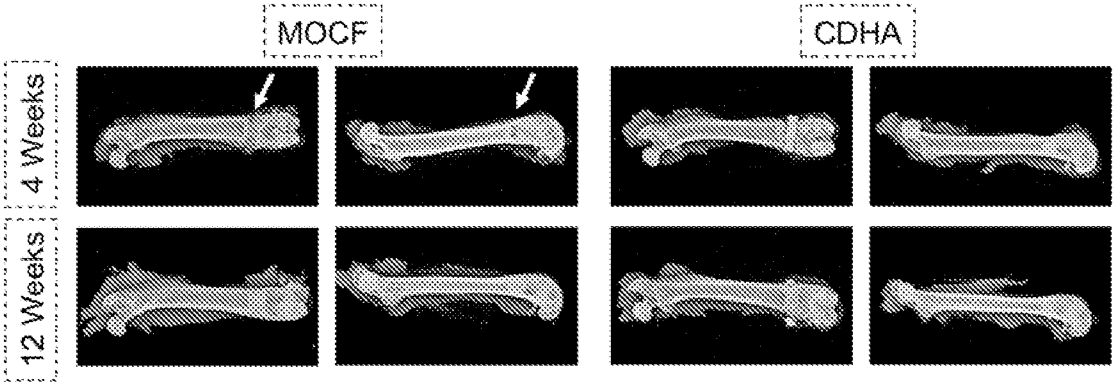
FIG. 27 presents representative radiographs of the femora implanted with MOCF or CDHA acquired at weeks 4 or 12 post operation. The distal femoral defect is marked with arrows.
Figure 28:
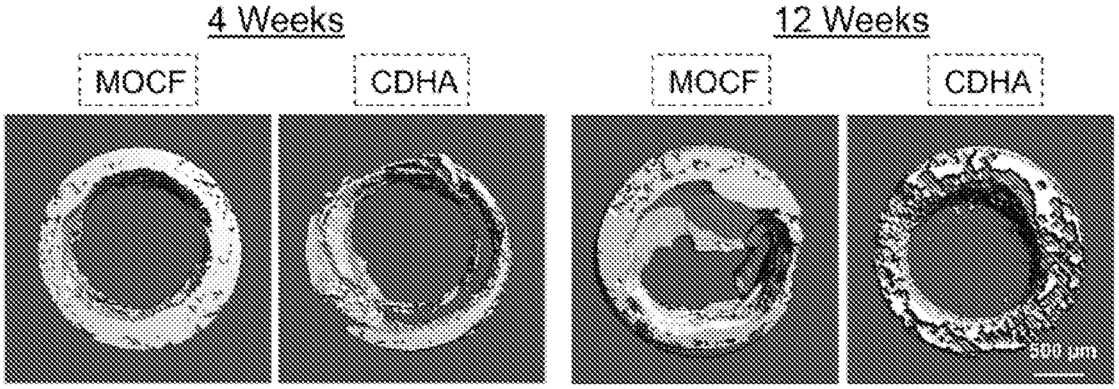
FIG. 28 presents representative micro computed tomography (micro-CT) images of the femoral defects in the MOCF and CDHA groups at weeks 4 and 12 post operation.
Figure 29:
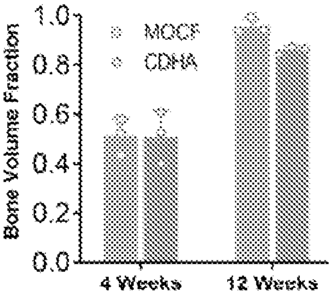
FIG. 29 is a graph plotting results of a quantitative analysis of bone volume fraction (bone volume/total volume, BV/TV) at the defect sites at weeks 4 and 12 post operation (n=3). All quantitative data are presented as mean±SD. Two-way ANOVA with Sidak's post hoc test was used.
Figure 30:
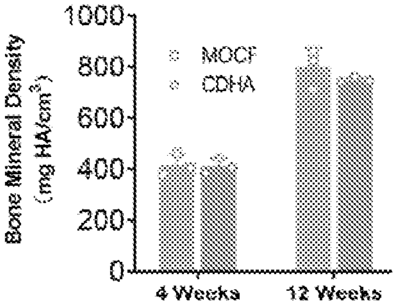
FIG. 30 is a graph plotting results of a quantitative analysis of bone mineral density (BMD) at the defect sites at weeks 4 and 12 post operation (n=3). All quantitative data are presented as mean±SD. Two-way ANOVA with Sidak's post hoc test was used.
Figure 31:
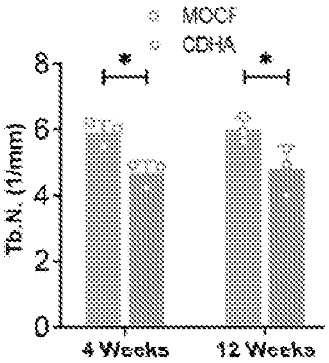
FIG. 31 is a graph plotting results of a quantitative analysis of trabecular number (Tb. N) at the defect sites at weeks 4 and 12 post operation (n=3). All quantitative data are presented as mean±SD. *P<0.05. Two-way ANOVA with Sidak's post hoc test was used.

At weeks 4 and 12 post operation, favorable osseointegration of both MOCF and CDHA along the defect edges could be observed from the radiographs, where the MOCF group displayed a remarkable bone thickening surrounding the defect edges (FIG. 27). Representative micro-CT images and the corresponding quantitative analysis revealed a magnified new bone area as well as higher bone volume/total volume (BV/TV) and bone mineral density (BMD) in the MOCF group compared to the CDHA group at week 12 post operation (FIGS. 28-30). Additionally, significantly more trabecular bone structures were formed in the MOCF group than in the CDHA group at weeks 4 and 12 post operation (FIG. 31). These results demonstrate the improved regenerative efficacy of the provided porous MOCF-derived scaffold relative to that of the traditional bio-cement, CDHA, showing the great potential of the MOCF-derived scaffold for clinical translational applications in treating osteoporotic bone disorders.

As used herein, the terms "about" and "approximately equal to," when used to modify a numerical value, indicate a defined range around that value. If "X" is the value, then "about X" or "approximately equal to X" includes values from 0.90X to 1.10X. Any reference to "about X" thus indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X.

As used herein, the terms "including," "comprising," "having," "containing," and variations thereof, are inclusive and open-ended and do not exclude additional, unrecited elements or method steps beyond those explicitly recited. As used herein, the phrase "consisting of" is closed and excludes any element, step, or ingredient not explicitly specified. As used herein, the phrase "consisting essentially of" limits the scope of the described feature to the specified materials or steps and those that do not materially affect the basic and novel characteristics of the disclosed feature.

Although the foregoing disclosure has been described in some detail by way of illustration and example for purpose of clarity of understanding, one of skill in the art will appreciate that certain changes and modifications within the spirit and scope of the disclosure may be practiced, e.g., within the scope of the appended claims. It should also be understood that aspects of the disclosure and portions of various recited embodiments and features can be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the disclosure. In addition, each reference provided herein is incorporated by reference in its entirety for all purposes to the same extent as if each reference was individually incorporated by reference.

What is claimed is:

1. A composition having a form of a Pickering foam and comprising:

15 wt % to 70 wt % magnesium oxide;

2 wt % to 10 wt % magnesium chloride;

0.2 wt % to 2 wt % of a surface modifying agent;

a calcium posphate cement, wherein the calcium posphate cement is calcium-deficient hydroxyapatite, hydroxyapatite, or brushite; and 20 wt % to 65 wt % water;

wherein the identity and amount of the surface modifying agent are effective to modify at least a portion of the magnesium oxide, thereby creating particulates sufficient to stabilize the composition in the form of the Pickering foam.

2. The composition of claim 1, wherein the surface modifying agent is a short-chain amphiphilic compound.

3. The composition of claim 1, wherein the molar ratio of the magnesium oxide to the magnesium chloride is between 2.5:1 and 15:1.

4. The composition of claim 1, wherein the molar ratio of the water to the magnesium chloride is between 5:1 and 25:1.

5. The composition of claim 1, further comprising a soluble phosphate compound.

6. The composition of claim 5, wherein the concentration of the soluble phosphate compound in the composition is between 0.1 wt % and 2 wt %.

7. The composition of claim 5, having the form of a homogeneous paste.

8. A cement, wherein the cement is formed by curing the homogeneous paste of claim 7, and wherein the cement comprises a plurality of pores.

9. The cement of claim 8, wherein at least 10% of the plurality of pores each independently has a diameter greater than 50 μm.

10. A bone repair scaffold comprising the cement of claim 8.

11. A method for repairing a bone defect in a subject, the method comprising implanting the bone repair scaffold of claim 10 in the subject proximate to the bone defect.

12. The composition of claim 1, further comprising gelatin or chitosan.

13. The composition of claim 12, wherein the concentration of the gelatin or chitosan in the composition is between 1 wt % and 10 wt %.

14. The composition of claim 1, wherein the concentration of the calcium phosphate cement is between 10 wt % and 35 wt %.

* * * * *

SEQUENCE LISTING

```
Sequence total quantity: 8
SEQ ID NO: 1            moltype = DNA  length = 22
FEATURE                 Location/Qualifiers
misc_feature            1..22
                        note = Description of sequence: Primer, name: Opn - F
source                  1..22
                        mol_type = other DNA
                        organism = synthetic construct
SEQUENCE: 1
agcaagaaac tcttccaagc aa                                              22

SEQ ID NO: 2            moltype = DNA  length = 23
FEATURE                 Location/Qualifiers
misc_feature            1..23
                        note = Description of sequence: Primer, name: Opn - R
source                  1..23
                        mol_type = other DNA
                        organism = synthetic construct
SEQUENCE: 2
gtgagattcg tcagattcat ccg                                             23

SEQ ID NO: 3            moltype = DNA  length = 19
FEATURE                 Location/Qualifiers
misc_feature            1..19
                        note = Description of sequence: Primer, name: Sp7 - F
source                  1..19
                        mol_type = other DNA
                        organism = synthetic construct
SEQUENCE: 3
gagcaaacat cagcgcacc                                                  19

SEQ ID NO: 4            moltype = DNA  length = 22
FEATURE                 Location/Qualifiers
misc_feature            1..22
                        note = Description of sequence: Primer, name: Sp7 - R
source                  1..22
                        mol_type = other DNA
                        organism = synthetic construct
SEQUENCE: 4
gcggctgatt ggcttcttct tc                                              22

SEQ ID NO: 5            moltype = DNA  length = 20
FEATURE                 Location/Qualifiers
misc_feature            1..20
                        note = Description of sequence: Primer, name: Runx2 - F
source                  1..20
```

-continued

```
                        mol_type = other DNA
                        organism = synthetic construct
SEQUENCE: 5
gccttcaagg ttgtagccct                                                20

SEQ ID NO: 6            moltype = DNA  length = 20
FEATURE                 Location/Qualifiers
misc_feature            1..20
                        note = Description of sequence: Primer, name: Runx2 -R
source                  1..20
                        mol_type = other DNA
                        organism = synthetic construct
SEQUENCE: 6
tgaacctggc cacttggttt                                                20

SEQ ID NO: 7            moltype = DNA  length = 20
FEATURE                 Location/Qualifiers
misc_feature            1..20
                        note = Description of sequence: Primer, name: Gapdh - F
source                  1..20
                        mol_type = other DNA
                        organism = synthetic construct
SEQUENCE: 7
catggccttc cgtgttccta                                                20

SEQ ID NO: 8            moltype = DNA  length = 22
FEATURE                 Location/Qualifiers
misc_feature            1..22
                        note = Description of sequence: Primer, name: Gapdh - R
source                  1..22
                        mol_type = other DNA
                        organism = synthetic construct
SEQUENCE: 8
cctgcttcac caccttcttg at                                             22
```